United States Patent
Lee et al.

(10) Patent No.: US 9,670,240 B2
(45) Date of Patent: Jun. 6, 2017

(54) CYCLIC PHOSPHINATE DERIVATIVES AND METHOD OF PREPARING THE SAME

(71) Applicant: KNU-INDUSTRY COOPERATION FOUNDATION, Chuncheon-si, Gangwon-do (KR)

(72) Inventors: Phil Ho Lee, Chuncheon-si (KR); Seo Hyun Shin, Chuncheon-si (KR); Dong Jin Kang, Chuncheon-si (KR); Da Han Eom, Chuncheon-si (KR); Yea Rin Kim, Chuncheon-si (KR); Yeon Seok Jeong, Chuncheon-si (KR); Won Seok Choi, Chuncheon-si (KR)

(73) Assignee: Knu-Industry Cooperation Foundation, Chunsheon-si (KR)

( * ) Notice: Subject to any disclaimer, the term of this patent is extended or adjusted under 35 U.S.C. 154(b) by 0 days.

(21) Appl. No.: 15/286,408

(22) Filed: Oct. 5, 2016

(65) Prior Publication Data

US 2017/0022229 A1    Jan. 26, 2017

Related U.S. Application Data

(62) Division of application No. 14/598,143, filed on Jan. 15, 2015, now Pat. No. 9,487,547.

(30) Foreign Application Priority Data

May 2, 2014  (KR) .................. 10-2014-0053257

(51) Int. Cl.
C07F 9/6571  (2006.01)
C07F 9/6574  (2006.01)

(52) U.S. Cl.
CPC .... *C07F 9/657181* (2013.01); *C07F 9/65744* (2013.01); *C07F 9/657172* (2013.01)

(58) Field of Classification Search
CPC ............ C07F 9/657181; C07F 9/65744; C07F 9/657172
See application file for complete search history.

(56) References Cited

U.S. PATENT DOCUMENTS 4,219,510 A    8/1980  Miles

FOREIGN PATENT DOCUMENTS

SU           186747    *  7/1966

OTHER PUBLICATIONS

Ivanov et al. (Izvestiya Akademii Nauk SSSR, Seriya Khimicheskaya (1967), (1), 226). Abstract.*
Ivanov et al. (Izvestiya Akademii Nauk SSSR, Seriya Khimicheskaya (1967), (5), 1090-3). Abstract.*
Tang, W. et al., "New Chiral Phosphorus Ligands for Enantioselective Hydrogenation," Chemical Reviews, vol. 103, No. 8, Aug. 2003, Published Online Jun. 6, 2003, 42 pages.
Thasana, N. et al., "Copper(I)-Mediated and Microwave-Assisted Caryl-Ocarboxylic Coupling: Synthesis of Benzopyranones and Isolamellarin Alkaloids," Journal of Organic Chemistry, vol. 72, No. 24, Nov. 23, 2007, Published Online Nov. 2, 2007, 4 pages.
Keglevich, G. et al., "Platinum(II) complexes of 2-alkoxy-dibenzo[c.e][1,2]oxaphosphorines," Transition Metal Chemistry, vol. 33, No. 4, May 2008, Published Online Mar. 4, 2008, 6 pages.
Seo, J. et al., "Synthesis of Phosphaisocoumarins through Rhodium-Catalyzed Cyclization Using Alkynes and Arylphosphonic Acid Monoesters," Organic Letters, vol. 15, No. 13, Jul. 5, 2013, Published Online Jun. 21, 2013, 4 pages.
Ryu, T. et al., "Rhodium-Catalyzed Oxidative Cyclization of Arylphosphonic Acid Monoethyl Esters with Alkenes: Efficient Synthesis of Benzoxaphosphole 1-Oxides," Organic Letters, vol. 15, No. 15, Aug. 2, 2013, Published Online Jul. 25, 2013, 4 pages.
Eom, D. et al., "Palladium-Catalyzed C(sp2 and sp3)—H Activation/C—O Bond Formation: Synthesis of Benzoxaphosphole 1- and 2-Oxides," Organic Letters, vol. 15, No. 20, Oct. 18, 2013, Published Online Oct. 8, 2013, 4 pages.
Jeong, Y., "Palladium-Catalyszed C(sp2)—H Activation/C—O Bond Formation: Synthesis of Benzoxaphosphole 2-oxide," Master Thesis, Kangwon National University, Feb. 2014, 121 pages. (Submitted with English Language Abstract).

* cited by examiner

*Primary Examiner* — Bruck Kifle
(74) *Attorney, Agent, or Firm* — McCoy Russell LLP

(57) ABSTRACT

Provided are novel cyclic phosphinate derivatives and a method of preparing the same, and more particularly, cyclic phosphinate derivatives including benzoxaphosphole oxide derivatives and benzoxaphosphorin oxide derivatives, and a method of preparing the same. The cyclic phosphinate derivative according to the present invention may have pharmacological and physiological activities, be used as the basic skeleton of the natural material, and be used in development of a new drug, and synthesis of various medicines. In addition, with the method of preparing a cyclic phosphinate derivative according to the present invention, various cyclic phosphinate derivatives may be prepared with high yield through a simple synthetic process by performing an intramolecular carbon-oxygen coupling reaction on the phosphinic acid derivative in the presence of a palladium (Pd) catalyst, an oxidant, and a base.

10 Claims, No Drawings

CYCLIC PHOSPHINATE DERIVATIVES AND METHOD OF PREPARING THE SAME

CROSS-REFERENCE TO RELATED APPLICATIONS

The present application is a divisional application of U.S. patent application Ser. No. 14/598,143 entitled "Novel Cyclic Phosphinate Derivatives and Method of Preparing the Same," filed on Jan. 15, 2015, which claims priority under 35 U.S.C. §119 to Korean Patent Application No. 10-2014-0053257, filed on May 2, 2014, in the Korean Intellectual Property Office, the entire contents of each of which are hereby incorporated by reference in their entirety for all purposes.

TECHNICAL FIELD

The following disclosure relates to novel cyclic phosphinate derivatives and a method of preparing the same, and more particularly, to cyclic phosphinate derivatives including benzoxaphosphole oxide derivatives and benzoxaphosphorin oxide derivatives, and a method of preparing the same.

BACKGROUND

Heterocyclic compounds configure a basic skeleton of a natural material, and among them, organic phosphorus compounds have pharmacological and physiological activities, such that the organic phosphorus compounds are important compounds in pharmaceutical, material, and crop protection agent fields.

Among them, since benzoxaphosphole oxide compounds have physiological activities and may be used as an important raw material or intermediate in agricultural and material chemistry fields in addition to being used in synthesizing a new medicine, an interest in synthesis methods thereof have increased. Therefore, synthesis methods of benzoxaphosphole oxide derivatives as described above have been reported (Chem. Rev. 2003, 103, 3029). Up to now, the methods of synthesizing benzoxaphosphole oxide have a disadvantage in that benzoxaphosphole oxide is synthesized through several steps.

Meanwhile, a dibenzoxaphosphorin oxide derivative is a lactone derivative including phosphorus. It was known that uses of lactone are various, and various application methods and synthesis methods have been reported (*J. Org. Chem.* 2007, 72, 9379-9382). In addition, it has been well known that lactone has physiological activities, and since lactone is used as a basic skeleton of a natural material, even in the case in which phosphorus is contained, it is expected that the lactone derivative will have physiological activities or be variously applied through additional steps. However, the number of reported compounds in which phosphorus is contained is small, and particularly, there is no reported compound in which various substituents are contained (*Transition Met. Chem.* 2008, 33, 505-510). In addition, recently, research into a method of synthesizing a carbon-carbon, carbon-nitrogen, or carbon-oxygen bond by using various transition metal catalysts through a carbon-hydrogen bond activation reaction with a directing group has been conducted. This reaction is characterized in that various bonds may be introduced by interaction between the catalyst and the directing group without pre-functionalization. Recently, it has been reported that various bonds are formed by using a directing group containing phosphorus through the carbon-hydrogen bond activation reaction with a transition metal (*Org. Lett.* 2013, 15, 3358-3361; *Org. Lett.* 2013, 15, 3986-3989). In addition, a method of forming a carbon-oxygen bond to synthesize a cyclic compound is a good method of synthesizing a novel heterocyclic compound (*Org. Lett.* 2013, 15, 5210-5213).

However, the case of synthesizing a benzoxaphosphole oxide derivative and a dibenzoxaphosphorin oxide derivative by using the transition metal catalyst through the carbon-hydrogen bond activation reaction has not yet been reported. Therefore, it is important to develop an efficient C—H bond activation reaction using a directing group associated with phosphorus.

The present invention relates to a new method of synthesizing a benzoxaphosphole oxide derivative and a dibenzoxaphosphorin oxide derivative having a short reaction step. The method of preparing a benzoxaphosphole oxide derivative and a dibenzoxaphosphorin oxide derivative according to the present invention has an advantage in that benzoxaphosphole oxide derivatives and dibenzoxaphosphorin oxide derivatives in which various substituents are introduced by an intramolecular carbon-oxygen coupling reaction due to the carbon ($sp^2$ or $sp^3$)-hydrogen bond activation reaction may be prepared from a phosphinic acid derivative in the presence of a palladium catalyst.

SUMMARY

An embodiment of the present invention is directed to providing a novel cyclic phosphinate derivative having pharmacological and physiological activities.

Another embodiment of the present invention is directed to providing a method of preparing a novel cyclic phosphinate derivative.

In one general aspect, there is provided a cyclic phosphinate derivative represented by the following Chemical Formula 1.

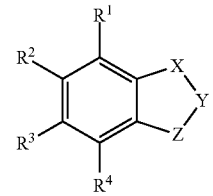

[Chemical Formula 1]

In Chemical Formula 1,
$R^1$ to $R^4$ are each independently hydrogen, (C1-C20)alkyl, halo(C1-C20)alkyl, (C1-C20)alkoxy, (C6-C20)aryl, halogen, (C6-C20)aryloxy, or tri(C1-C20)alkylsilyl; when X is

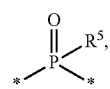

Y is O, or when X is O, Y is

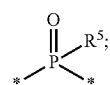

$R^5$ is (C1-C20)alkyl, (C1-C20)alkoxy or (C6-C20)aryl;
Z is —$CR^{11}R^{12}$— or —$CR^{13}$=$CR^{14}$—;
$R^{11}$ and $R^{12}$ are each independently hydrogen or (C1-C20) alkyl, or are linked to each other by (C1-C7)alkylene to form a spiro ring;
$R^{11}$ and $R^{12}$ are linked to each other by —$CR^{21}$=$CR^{22}$—$CR^{23}$=$CR^{24}$— or -L-$CR^{25}$=$CR^{26}$— to form a fused ring;
$R^{21}$ to $R^{26}$ are each independently hydrogen, (C1-C20)alkyl, halo(C1-C20)alkyl, (C1-C20)alkoxy, (C6-C20)aryl, or halogen, or are linked to a substituent adjacent thereto by (C1-C7)alkylene, (C2-C7)alkenylene, or (C4-C7)alkanedienylene to form a fused ring;
L is O or S; and
alkyl and aryl of $R^1$ to $R^5$ are further substituted with one or more substituents selected from the group consisting of halogen, (C1-C20)alkyl, (C1-C20)alkoxy, and halo(C1-C20)alkyl, respectively.

In another general aspect, there is provided a method of preparing a cyclic phosphinate derivative represented by Chemical Formula 1 characterized by performing an intramolecular carbon-oxygen coupling reaction on a phosphinic acid derivative represented by the following Chemical Formula 6 or 7 in the presence of a palladium (Pd) catalyst, an oxidant, and a base to prepare a cyclic phosphinate derivative represented by the following Chemical Formula 2 or 3.

[Chemical Formula 2]

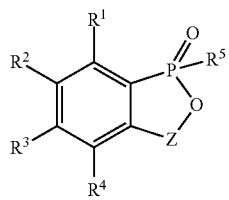

[Chemical Formula 3]

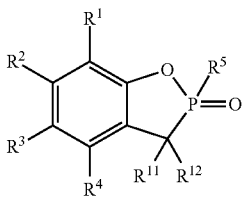

[Chemical Formula 6]

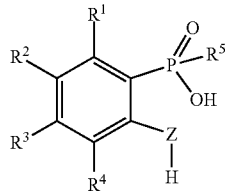

[Chemical Formula 7]

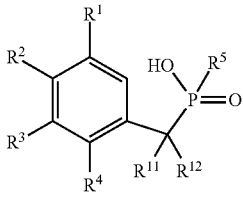

Hereinafter, the present invention will be described in detail.

Here, technical terms and scientific terms used in the present specification have the general meaning understood by those skilled in the art to which the present invention pertains unless otherwise defined. In addition, repetitive descriptions of the same technical configuration and action as those in the related art will be omitted.

The present invention may provide a cyclic phosphinate derivative represented by the following Chemical Formula 1:

[Chemical Formula 1]

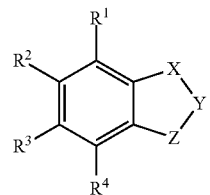

In Chemical Formula 1,
$R^1$ to $R^4$ are each independently hydrogen, (C1-C20)alkyl, halo(C1-C20)alkyl, (C1-C20)alkoxy, (C6-C20)aryl, halogen, (C6-C20)aryloxy, or tri(C1-C20)alkylsilyl;
when X is

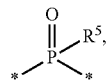

Y is O, or when X is O, Y is

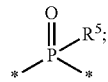

$R^5$ is (C1-C20)alkyl, (C1-C20)alkoxy or (C6-C20)aryl;
Z is —$CR^{11}R^{12}$— or —$CR^{13}$=$CR^{14}$—;
$R^{11}$ and $R^{12}$ are each independently hydrogen, or (C1-C20) alkyl, or are linked to each other by (C1-C7)alkylene to form a spiro ring;
$R^{13}$ and $R^{14}$ are linked to each other by —$CR^{21}$=$CR^{22}$—$CR^{23}$=$CR^{24}$— or -L-$CR^{25}$=$CR^{26}$— to form a fused ring;
$R^{21}$ to $R^{26}$ are each independently hydrogen, (C1-C20)alkyl, halo(C1-C20)alkyl, (C1-C20)alkoxy, (C6-C20)aryl, or halogen, or are linked to a substituent adjacent thereto by (C1-C7)alkylene, (C2-C7)alkenylene, or (C4-C7)alkanedienylene to form a fused ring;
L is O or S; and
alkyl and aryl of $R^1$ to $R^5$ are further substituted with one or more substituents selected from the group consisting of halogen, (C1-C20)alkyl, (C1-C20)alkoxy, and halo(C1-C20)alkyl, respectively.

The terms ⌈alkyl⌋ and ⌈alkoxy⌋ disclosed herein include both of the straight chain type and the branched chain type.

The term ⌈aryl⌋ disclosed herein, which is an organic radical derived from aromatic hydrocarbon by removing one hydrogen atom therefrom, includes a single ring or a fused ring containing, properly 4 to 7 ring atoms, and preferably 5 or 6 ring atoms in each ring, and include forms in which two or more aryls are combined through single bond(s). Specific examples of aryl include aromatic groups such as phenyl, naphthyl, biphenyl, indenyl, fluorenyl, phenanthrenyl, anthracenyl, triphenylenyl, pyrenyl, chrysenyl, and naphthacenyl.

The novel cyclic phosphinate derivative represented by Chemical Formula 1 may include a benzoxaphosphole oxide derivative and a benzoxaphosphorin oxide derivative, and may be, preferably, represented by the following Chemical Formula 2 or 3:

[Chemical Formula 2]

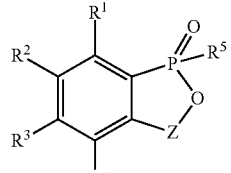

[Chemical Formula 3]

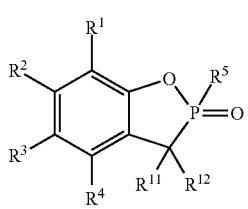

In Chemical Formulas 2 and 3, $R^1$ to $R^4$ and $R^5$ have the same definitions as defined in Chemical Formula 1;
Z is $CH_2$— or —$CR^{13}$=$CR^{14}$—;
$R^{11}$ and $R^{12}$ are each independently (C1-C20)alkyl, or are linked to each other by (C1-C7)alkylene to form a spiro ring; $R^{13}$ and $R^{14}$ are linked to each other by —$CR^{21}$=$CR^{22}$=$CR^{23}$=$C^{24}$— or -L-$CR^{25}$=$CR^{26}$— to form a fused ring;
$R^{21}$ to $R^{26}$ are each independently hydrogen, (C1-C20)alkyl, (C1-C20)alkoxy, (C6-C20)aryl, or halogen, or $R^{21}$ to $R^{24}$ are linked to a substituent adjacent thereto by (C1-C7)alkylene or (C4-C7)alkanedienylene to form a fused ring;
L is O or S; and
alkyl and aryl of $R^1$ to $R^5$ are further substituted with one or more substituents selected from the group consisting of halogen, (C1-C20)alkyl, (C1-C20)alkoxy, and halo(C1-C20)alkyl, respectively.

In detail, in Chemical Formulas 2 and 3, preferably, $R^1$ to $R^4$ may be each independently hydrogen, methyl, ethyl, propyl, butyl, pentyl, hexyl, trifluoromethyl, methoxy, ethoxy, propoxy, butoxy, pentyloxy, hexyloxy, phenyl, naphthyl, fluorenyl, chloro, bromo, fluoro, or trimethylsilyl (TMS), phenyl, naphthyl, or fluorenyl of $R^1$ to $R^4$ being further substituted with one or more substituents selected from the group consisting of chloro, bromo, fluoro, methyl, ethyl, propyl, butyl, pentyl, hexyl, methoxy, ethoxy, propoxy, butoxy, pentyloxy, hexyloxy, and trifluoromethyl; $R^5$ may be methyl, ethyl, propyl, butyl, pentyl, hexyl, methoxy, ethoxy, propoxy, butoxy, pentyloxy, hexyloxy, phenyl, or naphthyl, phenyl or naphthyl of $R^5$ being further substituted with one or more substituents selected from the group consisting of chloro, bromo, fluoro, methyl, ethyl, propyl, butyl, pentyl, hexyl, methoxy, ethoxy, propoxy, butoxy, pentyloxy, hexyloxy, and trifluoromethyl; Z may be —$CH_2$—,

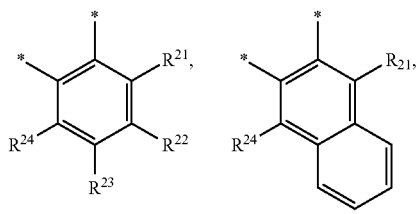

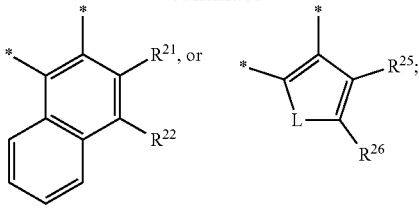

$R^{11}$ and $R^{12}$ may be each independently methyl, ethyl, propyl, butyl, pentyl, or hexyl, or be linked to each other by butylene or pentylene to form a Spiro ring; $R^{21}$ to $R^{26}$ may be each independently hydrogen, methyl, ethyl, propyl, butyl, pentyl, hexyl, methoxy, ethoxy, propoxy, butoxy, pentyloxy, hexyloxy, phenyl, naphthyl, chloro, bromo, or fluoro; and L may be O or S.

The cyclic phosphinate derivative according to the present invention may be selected from the following compounds, but is not limited thereto.

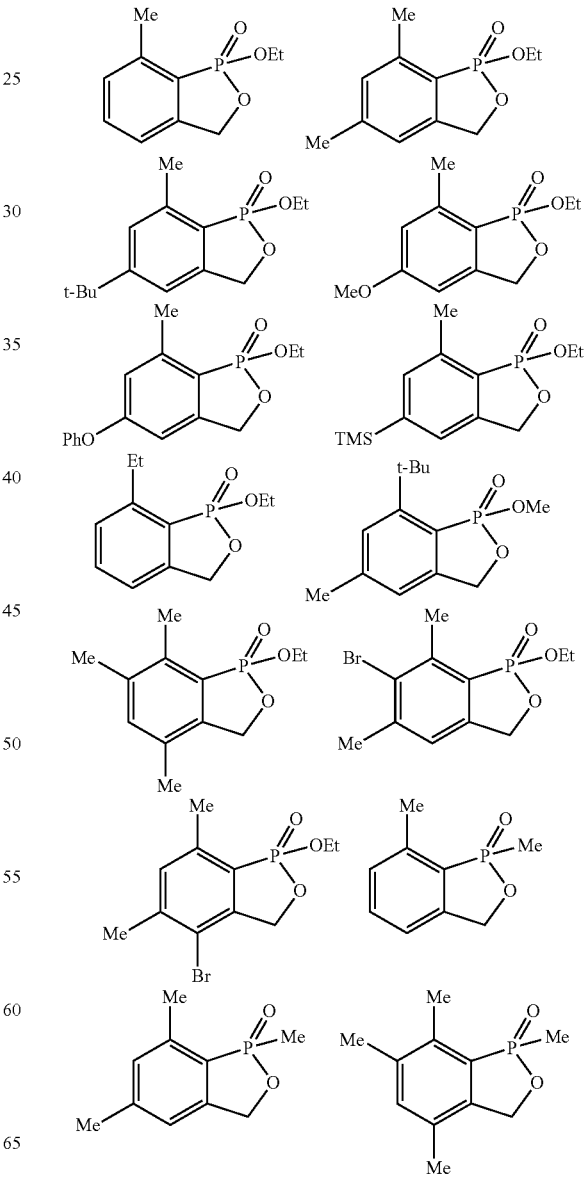

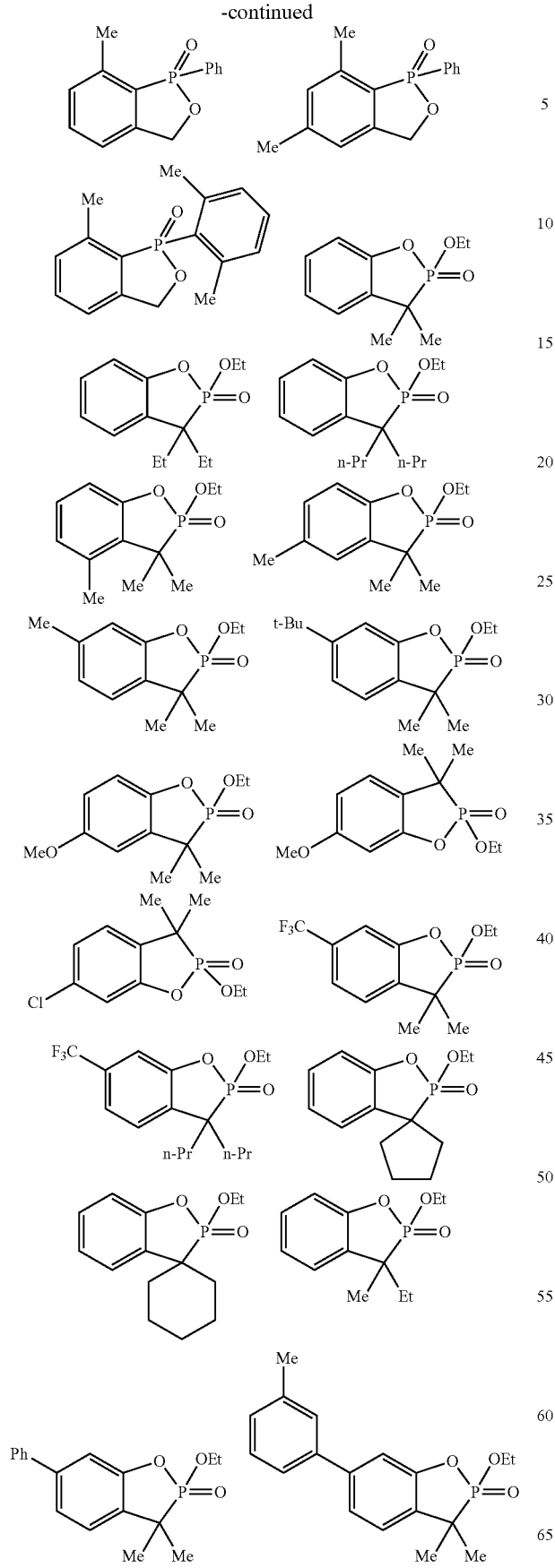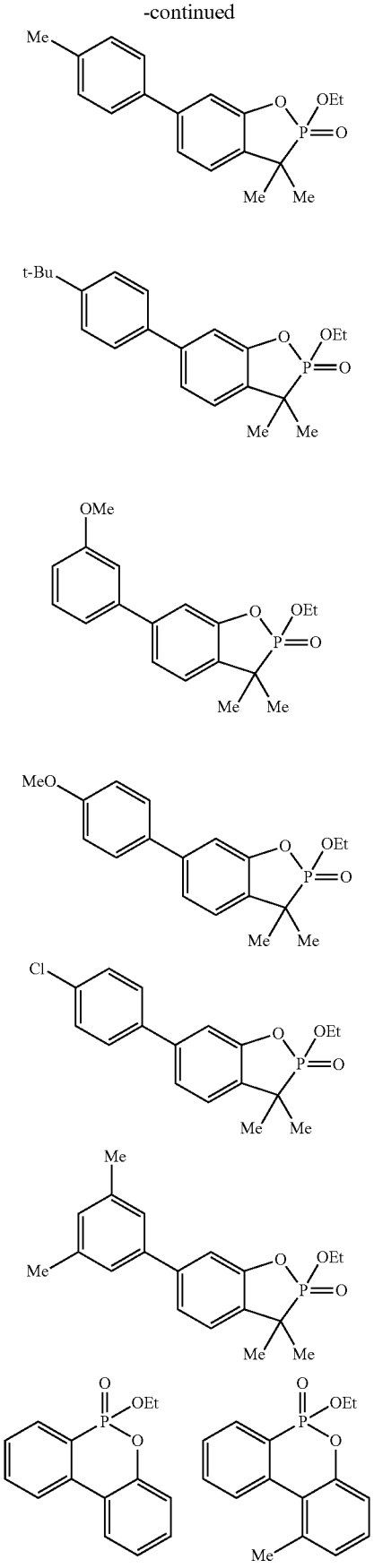

-continued

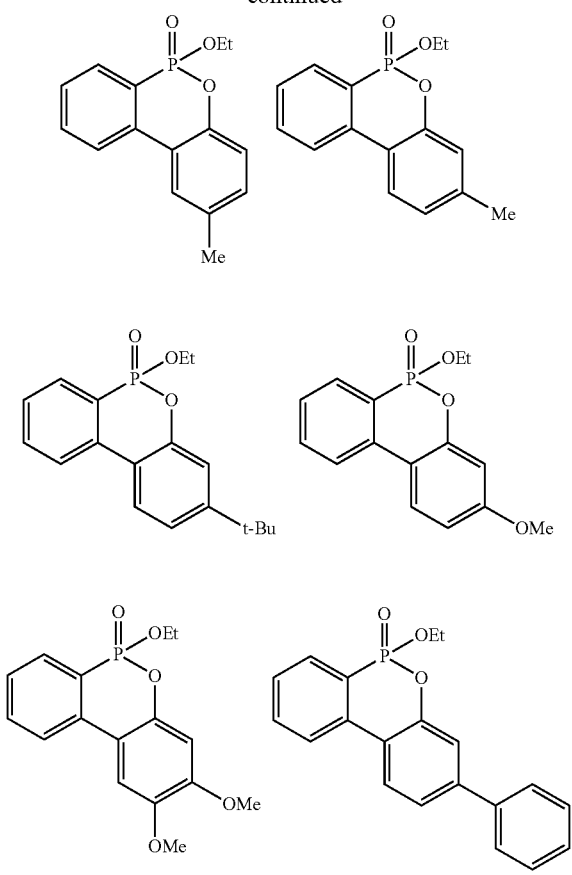

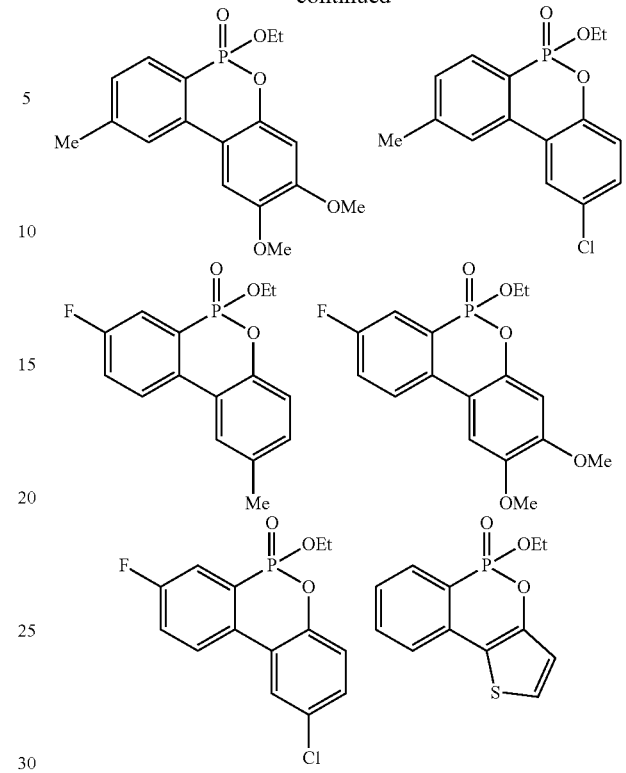

Hereinafter, the method of preparing a cyclic phosphinate derivative according to the present invention will be described in detail.

The present invention provides a method of preparing a cyclic phosphinate derivative characterized by performing an intramolecular carbon-oxygen coupling reaction on a phosphinic acid derivative represented by the following Chemical Formula 6 to prepare a cyclic phosphinate derivative represented by the following Chemical Formula 2 in the presence of a palladium (Pd) catalyst, an oxidant, and a base:

[Chemical Formula 2]

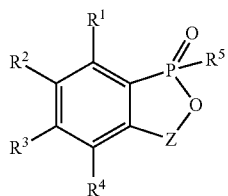

[Chemical Formula 6]

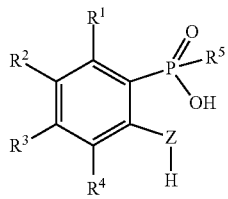

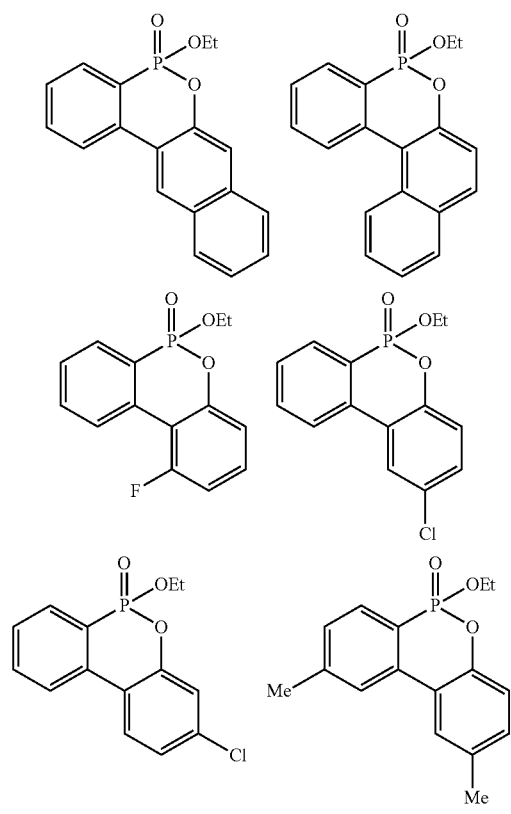

In Chemical Formulas 2 and 6,
$R^1$ to $R^4$ are each independently hydrogen, (C1-C20)alkyl, halo(C1-C20)alkyl, (C1-C20)alkoxy, (C6-C20)aryl, halogen, (C6-C20)aryloxy, or tri(C1-C20)alkylsilyl;

$R^5$ is (C1-C20)alkyl, (C1-C20)alkoxy, or (C6-C20)aryl;

Z is $CH_2$— or —$CR^{13}$=$CR^{14}$—;

$R^{13}$ and $R^{14}$ are linked to each other by —$CR^{21}$=$CR^{22}$—$CR^{23}$=$CR^{24}$— or -L-$CR^{25}$=$CR^{26}$— to form a fused ring;

$R^{21}$ to $R^{26}$ are each independently hydrogen, (C1-C20)alkyl, (C1-C20)alkoxy, (C6-C20)aryl, or halogen, or $R^{21}$ to $R^{24}$ are linked to a substituent adjacent thereto by (C1-C7)alkylene or (C4-C7)alkanedienylene to form a fused ring;

L is O or S; and alkyl and aryl of $R^1$ to $R^5$ are further substituted with one or more substituents selected from the group consisting of halogen, (C1-C20)alkyl, (C1-C20)alkoxy, and halo(C1-C20)alkyl, respectively.

In addition, the present invention provides a method of preparing a cyclic phosphinate derivative characterized by performing an intramolecular carbon-oxygen coupling reaction on a phosphinic acid derivative represented by the following Chemical Formula 7 to prepare a cyclic phosphinate derivative represented by the following Chemical Formula 3 in the presence of a palladium (Pd) catalyst, an oxidant, and a base:

[Chemical Formula 3]

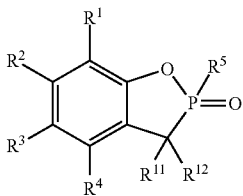

[Chemical Formula 7]

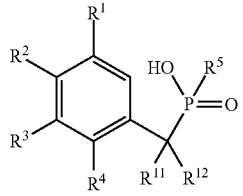

In Chemical Formulas 3 and 7, $R^1$ to $R^4$ are each independently hydrogen, (C1-C20)alkyl, halo(C1-C20)alkyl, (C1-C20)alkoxy, (C6-C20)aryl, halogen, (C6-C20)aryloxy, or tri(C1-C20)alkylsilyl;

$R^5$ is (C1-C20)alkyl, (C1-C20)alkoxy, or (C6-C20)aryl;

$R^{11}$ and $R^{12}$ are each independently (C1-C20)alkyl, or are linked to each other by (C1-C7)alkylene to form a spiro ring; and alkyl and aryl of $R^1$ to $R^5$ are further substituted with one or more substituents selected from the group consisting of halogen, (C1-C20)alkyl, (C1-C20)alkoxy, and halo(C1-C20)alkyl, respectively.

The method of preparing a cyclic phosphinate derivative represented by Chemical Formula 2 or 3 according to the present invention is a significantly effective method capable of obtaining a product with high yield and high purity by a simple process under mild conditions in the presence of the palladium (Pd) catalyst, the oxidant, and the base.

The palladium (Pd) catalyst used in the method of preparing a cyclic phosphinate derivative according to the present invention may be one or a mixture of two or more selected from the group consisting of $PdCl_2$, $PdBr_2$, $Pd(OAc)_2$, $Pd(dba)_2$, $Pd_2(dba)_3$, $Pd_2dba_3 \cdot CHCl_3$, $Pd(PPh_3)_4$, $Pd(OTf)_2$, $Pd(OTf)_2 \cdot 2H_2O$, $Pd(TFA)_2$, $PdCl_2(MeCN)_2$, $PdCl_2(PPh_3)_2$, $Pd(dppf)Cl_2$ and $[PdCl(C_3H_5)]_2$. More preferably, $Pd(OAc)_2$ may be used as the palladium (Pd) catalyst.

The palladium (Pd) catalyst used in the method of preparing a cyclic phosphinate derivative according to the present invention may be used in a range of 0.01 to 0.5 equivalents with respect to the phosphinic acid derivative represented by Chemical Formula 6 or 7. More preferably, the palladium (Pd) catalyst may be used in a range of 0.05 to 0.15 equivalents. In the case of using the palladium (Pd) catalyst in the above-mentioned range, the cyclic phosphinate derivative may be prepared with high yield, and in the case in which an amount of the palladium (Pd) catalyst is out of the range, yield and economic efficiency may be deteriorated.

As the oxidant used in the method of preparing a cyclic phosphinate derivative according to the present invention, one or a mixture of two or more selected from the group consisting of copper(I) chloride (CuCl), copper(I) oxide ($Cu_2O$), copper(II) oxide (CuO), copper(II) acetate (Cu(OAc)$_2$), copper triflate (Cu(OTf)$_2$), copper(II) chloride ($CuCl_2$), copper(I) bromide (CuBr), copper(I) iodide (CuI), copper(II) acetylacetonate (Cu(acac)$_2$), silver(II) oxide ($Ag_2O$), silver(I) oxide (AgO), silver acetate (AgOAc), silver(II) carbonate ($Ag_2CO_3$), sodium persulfate ($Na_2S_2O_8$), potassium persulfate ($K_2S_2O_8$), sodium acetate (NaOAc), benzoquinone (BQ), iron(III) chloride ($FeCl_3$), manganese(III) acetate dihydrate (Mn(OAc)$_3 \cdot 2H_2O$), vanadium(V) oxide ($V_2O_5$) iodosobenzene diacetate (PhI(OAc)$_2$), bis(trifluoroacetoxy)iodobenzene (PhI(TFA)$_2$), acetyl hypoiodite (IOAc), ozone, oxygen, $(PhCO_2)_2$, and 2,2,6,6-tetramethyl-1-piperidinyloxy (free radical, TEMPO) may be used. In view of reactivity and yield, it is most preferable that $Ag_2CO_3$, PhI(OAc)$_2$, or a mixture thereof is used as the oxidant.

The oxidant used in the method of preparing a cyclic phosphinate derivative according to the present invention may be used in a range of 0.1 to 5.0 equivalents with respect to the phosphinic acid derivative represented by Chemical Formula 6 or 7. In view of yield and economic efficiency, it is most preferable that 1.0 to 3.0 equivalents of the oxidant is used.

The base used in the method of preparing a cyclic phosphinate derivative according to the present invention may be one or a mixture of two or more selected from the group consisting of potassium phosphate monobasic [$KH_2PO_4$], sodium phosphate dibasic dihydrate [$Na_2HPO_4 \cdot 2H_2O$], sodium phosphate dibasic [$Na_2HPO_4$], sodium carbonate [$Na_2CO_3$], sodium phosphate monobasic [$NaH_2PO_4$], lithium acetate [LiOAc], lithium carbonate [$Li_2CO_3$], sodium acetate [NaOAc], potassium phosphate dibasic [$K_2HPO_4$], potassium phosphate tribasic [$K_3PO_4$], potassium carbonate [$K_2CO_3$], cesium fluoride [CsF], potassium bicarbonate [$KHCO_3$], potassium hydroxide [KOH], potassium fluoride [KF], potassium hexafluorophosphate [$KPF_6$], potassium acetate [KOAc], sodium fluoride [NaF], cesium acetate [CsOAc], cesium pivalate [CsOPiv], lithium hexafluorophosphate [$LiPF_6$], lithium phosphate [$Li_3PO_4$], lithium fluoride [LiF], and lithium iodide [LiI]. Preferably, NaOAc, $K_2HPO_4$, or KOAc may be used as the base.

The base used in the method of preparing a cyclic phosphinate derivative according to the present invention may be used in a range of 0.5 to 3.0 equivalents with respect to the phosphinic acid derivative represented by Chemical Formula 6 or 7. More preferably, the base may be used in a range of 1.0 to 2.5 equivalents.

In the method of preparing a cyclic phosphinate derivative according to the present invention, a ligand may be further used in order to prepare the cyclic phosphinate derivative represented by Chemical Formula 2, wherein the ligand may be one or a mixture of two or more selected from the group consisting of N-acetyl-L-leucine, Boc-Val-OH [N-(tert-butoxycarbonyl)-L-valine], N-Boc-L-isoleucine, Boc-L-leucine, Ac-Gly-OH [N-acetylglycine], N-Boc-L-isoleucine-hemihydrate, Ac-Ala-OH [N-acetyl-L-alanine], Ac-Phe-OH [N-acetyl-L-phenylalanine], pivalic acid, 2-methyl-2-phenylpropanoic acid, adamantane-1-carboxylic acid, (4-CF$_3$—C$_6$H$_4$)$_3$P, (4-MeO—C$_6$H$_4$)$_3$P, (4-MeO—C$_6$H$_4$)$_3$P, (2,6-di-MeO—C$_6$H$_3$)$_3$P, (2,4,6-tri-MeO—C$_6$H$_2$)$_3$P, Xantphos [4,5-Bis(diphenylphosphino)-9,9-dimethylxanthene], XPhos [2-Dicyclohexylphosphino-2',4',6'-triisopropylbiphenyl], CyJohnphos [(2-Biphenyl)dicyclohexylphosphine], SPhos [2-Dicyclohexylphosphino-2',6'-dimethoxybiphenyl], Johnphos [(2-Biphenyl)di-tert-butylphosphine], DPEphos [Bis[(2-diphenylphosphino)phenyl]ether], DPPP [1,3-Bis(diphenylphosphino)propane], DPPE [1,2-Bis(diphenylphosphino)ethane], DPPF [1,1'-Bis(diphenylphosphino) ferrocene], tri-o-tolylphosphine, and tri-2-furylphosphine. Preferably, N-acetyl-L-leucine or (4-MeO—C$_6$H$_4$)$_3$P may be used as the ligand.

The ligand used in the method of preparing a cyclic phosphinate derivative according to the present invention may be used in a range of 0.1 to 1.0 equivalent with respect to the phosphinic acid derivative represented by Chemical Formula 6. More preferably, the ligand may be used in a range of 0.1 to 0.5 equivalents.

As a solvent used in the method of preparing a cyclic phosphinate derivative according to the present invention, a general organic solvent may be used, but it is preferable that 1,4-dioxane, dichloromethane (DCM), dichloroethane (DCE), toluene, acetonitrile (MeCN), nitromethane, tetrahydrofuran (THF), chlorobenzene (PhCl), N,N-dimethylformamide (DMF), N,N-dimethylacetamide (DMA), t-butanol (t-BuOH), t-amylalcohol (t-AmOH), xylene, hexafluorobenzene (C$_6$F$_6$), bromobenzene (PhBr), trifluoroacetic acid, benzene, or a mixed solvent thereof is used. More preferably, dichloroethane (DCE), chlorobenzene (PhCl), or t-butanol (t-BuOH) may be used.

In the method of preparing a cyclic phosphinate derivative according to the present invention, any reaction temperature may be possible as long as it is a general temperature used in organic synthesis. However, the reaction temperature may be changed depending on a reaction time, a reactant, and an amount of a starting material, and in order to prevent the reaction time from being increased or a reaction yield from being deteriorated by generation of by-products, a cyclization reaction may be performed in a temperature range of room temperature to 160° C., and preferably 80 to 120° C.

The reaction time may be changed depending on the reactant, the amount of the reactant, and the kind and amount of solvent, and the reaction is terminated after confirming that the phosphinic acid derivative represented by Chemical Formula 6 or 7, which is the starting material, is completely consumed using thin layer chromatography (TLC), or the like. When the reaction is completed, after distilling the solvent under reduced pressure, a target material may be separated and purified by a general method such as column chromatography, or the like.

DETAILED DESCRIPTION OF EMBODIMENTS

Hereinafter, configurations of the present invention will be described in detail through Examples, but the following Examples are only to assist in understanding of the present invention. Therefore, the scope of the present invention is not limited thereto.

[Example 1] Preparation of 7-methyl-1-oxo-1-ethoxy-2,1-benzoxaphosphole

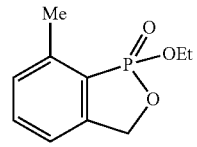 [SMILES: CCOP1(=O)OCc2cccc(C)c21]

After Pd(OAc)$_2$ (4.5 mg, 10 mol %, 0.1 eq), (4-MeO—C$_6$H$_4$)$_3$P (28.2 mg, 0.08 mmol), Ag$_2$CO$_3$ (165.4 mg, 0.6 mmol), and K$_2$HPO$_4$ (87.2 mg, 0.5 mmol) were put into a V-vial, 2,6-dimethylphenyl-phosphonic acid monoethyl ester (42.8 mg, 0.2 mmol) as a starting material and PhCL (2.0 mL) as a solvent were added thereto and stirred at 120° C. for 12 hours. After confirming that the starting material was completely consumed using TLC, the resultant was extracted with ethylacetate (5 mL×3) and the reaction was terminated by celite filtration. After removing the solvent, the resultant was separated using column chromatography, thereby obtaining 7-methyl-1-oxo-1-ethoxy-2,1-benzoxaphosphole (25.5 mg, 60%) corresponding to the target compound.

$^1$H NMR (400 MHz, CDCl$_3$) δ 7.49 (t, J=7.6 Hz, 1H), 7.26-7.23 (m, 1H), 7.13-7.11 (m, 1H), 5.29-5.16 (m, 2H), 4.22-4.09 (m, 2H), 2.59 (s, 3H), 1.35 (t, J=7.1 Hz, 3H)

[Example 2] Preparation of 5,7-dimethyl-1-oxo-1-ethoxy-2,1-benzoxaphosphole

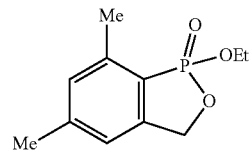 [SMILES: CCOP1(=O)OCc2cc(C)cc(C)c21]

A reaction was performed by the same method as in Example 1 except for using 2,4,6-trimethylphenyl-phosphonic acid monoethyl ester (45.6 mg, 0.2 mmol) instead of 2,6-dimethylphenyl-phosphonic acid monoethyl ester of Example 1, thereby obtaining 5,7-dimethyl-1-oxo-1-ethoxy-2,1-benzoxaphosphole (36.2 mg, 80%) corresponding to the target compound.

$^1$H NMR (400 MHz, CDCl$_3$) δ 7.06 (d, J=5.8 Hz, 1H), 6.92 (s, 1H), 5.23-5.11 (m, 2H), 4.21-4.03 (m, 2H), 2.54 (s, 3H), 2.39 (s, 3H), 1.34 (t, J=7.1 Hz, 3H)

[Example 3] Preparation of 5-tert-butyl-7-methyl-1-oxo-1-ethoxy-2,1-benzoxaphosphole

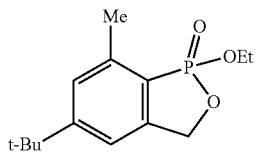

A reaction was performed by the same method as in Example 1 except for using 2,6-dimethyl-4-t-butylphenyl-phosphonic acid monoethyl ester (54.1 mg, 0.2 mmol) instead of 2,6-dimethylphenyl-phosphonic acid monoethyl ester of Example 1, thereby obtaining 5-tert-butyl-7-methyl-1-oxo-1-ethoxy-2,1-benzoxaphosphole (34.3 mg, 64%) corresponding to the target compound.

$^{1}$H NMR (400 MHz, CDCl$_{3}$) δ 7.26 (d, J=5.8 Hz, 1H), 7.10 (s, 1H), 5.27-5.14 (m, 2H), 4.22-4.06 (m, 2H), 2.57 (s, 3H), 1.35 (d, J=7.1 Hz, 3H), 1.32 (s, 9H)

[Example 4] Preparation of 5-methoxy-7-methyl-1-oxo-1-ethoxy-2,1-benzoxaphosphole

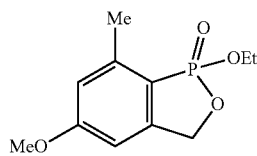 [SMILES: CCOP1(=O)OCc2cc(C(C)(C)C)cc(C)c21]

A reaction was performed by the same method as in Example 1 except for using 2,6-dimethyl-4-methoxyphenyl-phosphonic acid monoethyl ester (48.8 mg, 0.2 mmol) instead of 2,6-dimethylphenyl-phosphonic acid monoethyl ester of Example 1, thereby obtaining 5-methoxy-7-methyl-1-oxo-1-ethoxy-2,1-benzoxaphosphole (30.0 mg, 62%) corresponding to the target compound.

$^{1}$H NMR (400 MHz, CDCl$_{3}$) δ 6.70 (d, J=4.0 Hz, 1H), 6.51 (s, 1H), 5.16-5.03 (m, 2H), 4.12-3.98 (m, 2H), 3.80 (s, 3H), 2.47 (s, 3H), 1.27 (t, J=7.1 Hz, 3H)

[Example 5] Preparation of 5-phenoxy-7-methyl-1-oxo-1-ethoxy-2,1-benzoxaphosphole

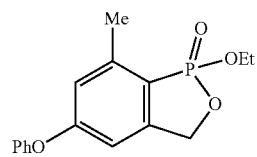 [SMILES: CCOP1(=O)OCc2cc(Oc3ccccc3)cc(C)c21]

A reaction was performed by the same method as in Example 1 except for using 2,6-dimethyl-4-phenoxyphenyl-phosphonic acid monoethyl ester (61.3 mg, 0.2 mmol) instead of 2,6-dimethylphenyl-phosphonic acid monoethyl ester of Example 1, thereby obtaining 5-phenoxy-7-methyl-1-oxo-1-ethoxy-2,1-benzoxaphosphole (36.5 mg, 60%) corresponding to the target compound.

$^{1}$H NMR (400 MHz, CDCl$_{3}$) δ 7.40 (t, J=7.9 Hz, 2H), 7.21 (t, J=7.9 Hz, 1H), 7.06-7.03 (m, 2H), 6.86-6.85 (m, 1H), 6.61 (s, 1H), 5.19-5.07 (m, 2H), 4.22-4.09 (m, 2H), 2.53 (s, 3H), 1.36 (t, J=7.1 Hz, 3H)

[Example 6] Preparation of 5-(trimethylsilyl)-7-methyl-1-oxo-1-ethoxy-2,1-benzoxaphosphole

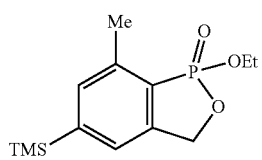 [SMILES: CCOP1(=O)OCc2cc([Si](C)(C)C)cc(C)c21]

A reaction was performed by the same method as in Example 1 except for using 2,6-dimethyl-4-trimethylsilyl-phenyl-phosphonic acid monoethyl ester (57.3 mg, 0.2 mmol) instead of 2,6-dimethylphenyl-phosphonic acid monoethyl ester of Example 1, thereby obtaining 5-(trimethylsilyl)-7-methyl-1-oxo-1-ethoxy-2, 1-benzoxaphosphole (30.1 mg, 53%) corresponding to the target compound.

$^{1}$H NMR (400 MHz, CDCl$_{3}$) δ 7.36 (d, J=6.4 Hz, 1H), 7.25 (d, J=3.0 Hz, 1H), 5.30-5.17 (m, 2H), 4.18-4.11 (m, 2H), 2.59 (s, 3H), 1.35 (t, J=7.1 Hz, 3H), 0.28 (s, 9H)

[Example 7] Preparation of 7-ethyl-1-oxo-1-ethoxy-2,1-benzoxaphosphole

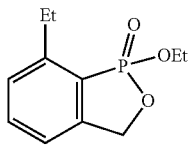 [SMILES: CCOP1(=O)OCc2cccc(CC)c21]

A reaction was performed by the same method as in Example 1 except for using 2-methyl-6-ethylphenyl-phosphonic acid monoethyl ester (45.6 mg, 0.2 mmol) instead of 2,6-dimethylphenyl-phosphonic acid monoethyl ester of Example 1, thereby obtaining 7-ethyl-1-oxo-1-ethoxy-2,1-benzoxaphosphole (19.5 mg, 43%) corresponding to the target compound.

$^{1}$H NMR (400 MHz, CDCl$_{3}$) δ 7.52 (td, J$_{1}$=11.4, J$_{2}$=1.2 Hz, 1H), 7.29 (t, J=6.9 Hz, 1H), 7.14-7.11 (m, 1H), 5.29-5.16 (m, 2H), 4.23-4.08 (m, 2H), 2.93 (q, J=7.6 Hz, 2H), 1.34 (t, J=7.7 Hz, 6H)

[Example 8] Preparation of 7-tert-butyl-5-methyl-1-oxo-1-methoxy-2,1-benzoxaphosphole

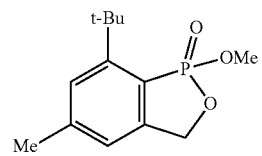 [SMILES: COP1(=O)OCc2cc(C)cc(C(C)(C)C)c21]

A reaction was performed by the same method as in Example 1 except for using 2,4-dimethyl-6-t-butylphenyl-phosphonic acid monoethyl ester (51.3 mg, 0.2 mmol) instead of 2,6-dimethylphenyl-phosphonic acid monoethyl ester of Example 1, thereby obtaining 7-tert-butyl-5-methyl-1-oxo-1-methoxy-2,1-benzoxaphosphole (28.5 mg, 56%) corresponding to the target compound.

$^{1}$H NMR (400 MHz, CDCl$_{3}$) δ 7.29 (d, J=6.8 Hz, 1H), 6.93 (s, 1H), 5.22-5.12 (m, 2H), 3.71 (d, J=11.9 Hz, 3H), 2.41 (s, 3H), 1.51 (s, 9H)

[Example 9] Preparation of 4,6,7-trimethyl-1-oxo-1-ethoxy-2,1-benzoxaphosphole

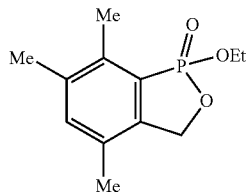 [SMILES: CCOP1(=O)OCc2c(C)cc(C)c(C)c21]

A reaction was performed by the same method as in Example 1 except for using 2,3,5,6-tetramethylphenyl-phosphonic acid monoethyl ester (48.5 mg, 0.2 mmol) instead of 2,6-dimethylphenyl-phosphonic acid monoethyl ester of Example 1, thereby obtaining 4,6,7-trimethyl-1-oxo-1-ethoxy-2,1-benzoxaphosphole (25.9 mg, 54%) corresponding to a target compound.

$^1$H NMR (400 MHz, CDCl$_3$) δ 7.15 (s, 1H), 5.18-5.04 (m, 2H), 4.21-4.05 (m, 2H), 2.46 (s, 3H), 2.29 (s, 3H), 2.16 (s, 3H), 1.34 (t, J=7.1 Hz, 3H)

[Example 10] Preparation of 6-bromo-5,7-dimethyl-1-oxo-1-ethoxy-2,1-benzoxaphosphole and 4-bromo-5,7-dimethyl-1-oxo-1-ethoxy-2,1-benzoxaphosphole

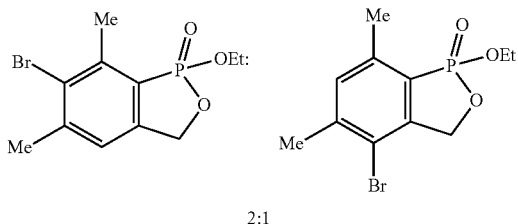

2:1

A reaction was performed by the same method as in Example 1 except for using 3-bromo-2,4,6-trimethylphenyl-phosphonic acid monoethyl ester (61.4 mg, 0.2 mmol) instead of 2,6-dimethylphenyl-phosphonic acid monoethyl ester of Example 1, thereby obtaining 6-bromo-5, 7-dim ethyl-1-oxo-1-ethoxy-2, 1-benzoxaphosphole and 4-bromo-5, 7-dim ethyl-1-oxo-1-ethoxy-2,1-benzoxaphosphole at a ratio of 2:1 (38.4 mg, 63%) corresponding to the target compounds.

6-Bromo-5,7-dimethyl-1-oxo-1-ethoxy-2,1-benzoxaphosphole: $^1$H NMR (400 MHz, CDCl$_3$) δ 7.04 (d, J=3.4 Hz, 1H), 5.20-5.07 (m, 2H), 4.23-4.07 (m, 2H), 2.64 (s, 3H), 2.49 (s, 3H), 1.35 (t, J=7.1 Hz, 3H)

4-Bromo-5,7-dimethyl-1-oxo-1-ethoxy-2,1-benzoxaphosphole: $^1$H NMR (400 MHz, CDCl$_3$) δ 7.15 (d, J=6.7 Hz, 1H), 5.15-5.02 (m, 2H), 4.19-4.09 (m, 2H), 2.51 (s, 3H), 2.44 (s, 3H), 1.35 (t, J=7.0 Hz, 3H)

[Example 11] Preparation of 7-methyl-1-oxo-1-methyl-2,1-benzoxaphosphole

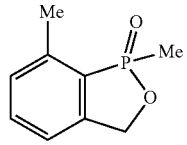 [SMILES: Cc1cccc2c1P(C)(=O)OC2]

A reaction was performed by the same method as in Example 1 except for using methyl-(2,6-dimethylphenyl)-phosphinic acid (36.8 mg, 0.2 mmol) instead of 2,6-dimethylphenyl-phosphonic acid monoethyl ester of Example 1, thereby obtaining 7-methyl-1-oxo-1-methyl-2,1-benzoxaphosphole (29.5 mg, 81%) corresponding to the target compound.

$^1$H NMR (400 MHz, CDCl$_3$) δ 7.48 (t, J=7.6 Hz, 1H), 7.24 (t, J=6.3 Hz, 1H), 7.14 (d, J=7.6 Hz, 1H), 5.46-5.21 (m, 2H), 2.62 (s, 3H), 1.84 (d, J=14.6 Hz, 3H)

[Example 12] Preparation of 5,7-dimethyl-1-oxo-1-methyl-2,1-benzoxaphosphole

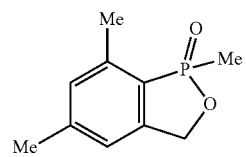 [SMILES: Cc1cc(C)c2c(c1)COP2(C)=O]

A reaction was performed by the same method as in Example 1 except for using methyl-(2,4,6-trimethylphenyl)-phosphinic acid (39.6 mg, 0.2 mmol) instead of 2,6-dimethylphenyl-phosphonic acid monoethyl ester of Example 1, thereby obtaining 5,7-dimethyl-1-oxo-1-methyl-2,1-benzoxaphosphole (34.1 mg, 87%) corresponding to the target compound.

$^1$H NMR (400 MHz, CDCl$_3$) δ 7.05 (d, J=5.0 Hz, 1H), 6.94 (s, 1H), 5.41-5.16 (m, 2H), 2.57 (s, 3H), 2.39 (s, 3H), 1.81 (d, J=14.6 Hz, 3H)

[Example 13] Preparation of 4,6,7-trimethyl-1-oxo-1-methyl-2,1-benzoxaphosphole

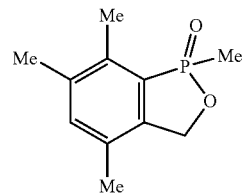

A reaction was performed by the same method as in Example 1 except for using methyl-(2,3,5,6-tetramethylphenyl)-phosphinic acid (42.4 mg, 0.2 mmol) instead of 2,6-dimethylphenyl-phosphonic acid monoethyl ester of Example 1, thereby obtaining 4,6,7-trimethyl-1-oxo-1-methyl-2,1-benzoxaphosphole (23.5 mg, 56%) corresponding to the target compound.

¹H NMR (400 MHz, CDCl₃) δ 7.14 (s, 1H), 5.35-5.10 (m, 2H), 2.49 (s, 3H), 2.29 (s, 3H), 2.18 (s, 3H), 1.81 (d, J=14.5 Hz, 3H)

[Example 14] Preparation of 7-methyl-1-oxo-1-phenyl-2,1-benzoxaphosphole

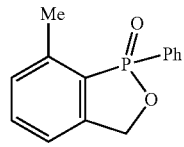 [SMILES: Cc1cccc2c1P(=O)(c1ccccc1)OC2]

A reaction was performed by the same method as in Example 1 except for using phenyl-(2,6-dimethylphenyl)-phosphinic acid (49.2 mg, 0.2 mmol) instead of 2,6-dimethylphenyl-phosphonic acid monoethyl ester of Example 1, thereby obtaining 7-methyl-1-oxo-1-phenyl-2,1-benzoxaphosphole (28.3 mg, 58%) corresponding to the target compound.

¹H NMR (400 MHz, CDCl₃) δ 7.76-7.70 (m, 2H), 7.58-7.44 (m, 3H), 7.23-7.17 (m, 2H), 5.62-5.39 (m, 2H), 2.36 (s, 3H)

[Example 15] Preparation of 5,7-dimethyl-1-oxo-1-phenyl-2,1-benzoxaphosphole

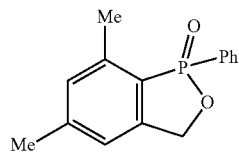 [SMILES: Cc1cc(C)c2c(c1)COP2(=O)c1ccccc1]

A reaction was performed by the same method as in Example 1 except for using phenyl-(2,4,6-trimethylphenyl)-phosphinic acid (52.1 mg, 0.2 mmol) instead of 2,6-dimethylphenyl-phosphonic acid monoethyl ester of Example 1, thereby obtaining 5,7-dimethyl-1-oxo-1-phenyl-2,1-benzoxaphosphole (32.0 mg, 62%) corresponding to the target compound.

¹H NMR (400 MHz, CDCl₃) δ 7.74-7.69 (m, 2H), 7.56-7.52 (m, 1H), 7.47-7.43 (m, 2H), 7.01-7.00 (m, 2H), 5.56-5.33 (m, 2H), 2.40 (s, 3H), 2.32 (s, 3H)

[Example 16] Preparation of 7-methyl-1-oxo-1-(2,6-dimethylphenyl)-2,1-benzoxaphosphole

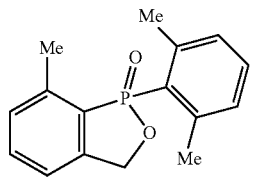 [SMILES: Cc1cccc(C)c1P1(=O)OCc2cccc(C)c21]

A reaction was performed by the same method as in Example 1 except for using bis(2,6-dimethylphenyl)-phosphinic acid (54.9 mg, 0.2 mmol) instead of 2,6-dimethylphenyl-phosphonic acid monoethyl ester of Example 1, thereby obtaining 7-methyl-1-oxo-1-(2,6-dimethylphenyl)-2,1-benzoxaphosphole (12.0 mg, 22%) corresponding to the target compound.

¹H NMR (400 MHz, CDCl₃) δ 7.46 (td, J₁=7.5, J₂=1.0 Hz, 1H), 7.31 (td, J₁=15.2, J₂=1.6 Hz, 1H), 7.20-7.15 (m, 2H), 7.11-7.07 (m, 2H), 5.68-5.33 (m, 2H), 2.43 (s, 6H), 2.28 (s, 3H)

[Example 17] Preparation of 3,3-dimethyl-2-oxo-2-ethoxy-1,2-benzoxaphosphole

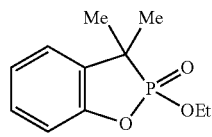 [SMILES: CCOP1(=O)Oc2ccccc2C1(C)C]

After Pd(OAc)₂ (4.5 mg, 10 mol %, 0.1 eq), PhI(OAc)₂ (99.6 mg, 0.3 mmol), and NaOAc (16.4 mg, 0.2 mmol) were put into a V-vial, dimethylbenzylphosphonic acid monoethyl ester (45.6 mg, 0.2 mmol) as a starting material and DCE (2.0 mL) as a solvent were added thereto and stirred at 80° C. for 20 hours. After confirming that the starting material was completely consumed using TLC, the resultant was extracted with ethylacetate (5 mL×3) and the reaction was terminated by celite filtration. After removing the solvent, the resultant was separated using column chromatography, thereby obtaining 3,3-dimethyl-2-oxo-2-ethoxy-1,2-benzoxaphosphole (39.4 mg, 87%) corresponding to the target compound.

¹H NMR (400 MHz, CDCl₃) δ 7.24-7.16 (m, 2H), 7.11-7.06 (m, 1H), 7.01-6.99 (m, 1H), 4.35-4.26 (m, 2H), 1.52 (dd, J=17.6, 3.9 Hz, 6H), 1.36 (t, J=7.1 Hz, 3H)

[Example 18] Preparation of 3,3-diethyl-2-oxo-2-ethoxy-1,2-benzoxaphosphole

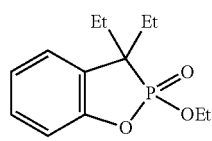 [SMILES: CCOP1(=O)Oc2ccccc2C1(CC)CC]

A reaction was performed by the same method as in Example 17 except for using diethylbenzylphosphonic acid monoethyl ester (51.3 mg, 0.2 mmol) instead of dimethylbenzylphosphonic acid monoethyl ester of Example 17, thereby obtaining 3,3-diethyl-2-oxo-2-ethoxy-1,2-benzoxaphosphole (44.2 mg, 87%) corresponding to the target compound.

¹H NMR (400 MHz, CDCl₃) δ 7.24-7.20 (m, 1H), 7.12-7.05 (m, 2H), 7.01-7.00 (m, 1H), 4.36-4.23 (m, 2H), 2.07-1.18 (m, 4H), 1.35 (t, J=7.4 Hz, 3H), 1.09 (t, J=7.4 Hz, 3H), 0.89 (t, J=7.4 Hz, 3H)

[Example 19] Preparation of 3,3-dipropyl-2-oxo-2-ethoxy-1,2-benzoxaphosphole

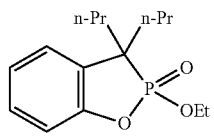

A reaction was performed by the same method as in Example 17 except for using dipropylbenzylphosphonic acid monoethyl ester (48.0 mg, 0.2 mmol) instead of dimethylbenzylphosphonic acid monoethyl ester of Example 17, thereby obtaining 3,3-dipropyl-2-oxo-2-ethoxy-1,2-benzoxaphosphole (54.2 mg, 96%) corresponding to the target compound.

$^1$H NMR (400 MHz, CDCl$_3$) δ 7.24-7.19 (m, 1H), 7.13-7.11 (m, 1H), 7.08-7.04 (m, 1H), 7.00-6.98 (m, 1H), 4.35-4.21 (m, 2H), 2.00-1.55 (m, 5H), 1.48-1.37 (m, 2H), 1.34 (t, J=7.1 Hz, 3H), 1.21-1.08 (m, 1H), 0.99 (t, J=7.2 Hz, 3H), 0.86 (t, J=7.3 Hz, 3H)

[Example 20] Preparation of 3,3-dimethyl-2-oxo-2-ethoxy-4-methyl-1,2-benzoxaphosphole

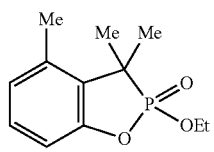 [SMILES: CCOP1(=O)Oc2cccc(C)c2C1(C)C]

A reaction was performed by the same method as in Example 17 except for using 2-(methyl)-dimethylbenzylphosphonic acid monoethyl ester (48.5 mg, 0.2 mmol) instead of dimethylbenzylphosphonic acid monoethyl ester of Example 17, thereby obtaining 3,3-dimethyl-2-oxo-2-ethoxy-4-methyl-1,2-benzoxaphosphole (28.8 mg, 60%) corresponding to the target compound.

$^1$H NMR (400 MHz, CDCl$_3$) δ 7.10 (t, J=7.9 Hz, 1H), 6.86-6.82 (m, 2H), 4.33-4.26 (m, 2H), 2.40 (s, 3H), 1.61 (dd, J=17.6, 15.1 Hz, 6H), 1.36 (t, J=7.1 Hz, 3H)

[Example 21] Preparation of 3,3-dimethyl-2-oxo-2-ethoxy-5-methyl-1,2-benzoxaphosphole

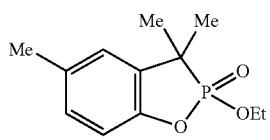 [SMILES: CCOP1(=O)Oc2ccc(C)cc2C1(C)C]

A reaction was performed by the same method as in Example 17 except for using 3-(methyl)-dimethylbenzylphosphonic acid monoethyl ester (48.5 mg, 0.2 mmol) instead of dimethylbenzylphosphonic acid monoethyl ester of Example 17, thereby obtaining 3,3-dimethyl-2-oxo-2-ethoxy-5-methyl-1,2-benzoxaphosphole (34.1 mg, 71%) corresponding to the target compound.

$^1$H NMR (400 MHz, CDCl$_3$) δ 7.02-6.97 (m, 2H), 6.89 (d, J=8.1 Hz, 1H), 4.34-4.24 (m, 2H), 2.31 (s, 3H), 1.50 (dd, J=17.6, 3.9 Hz, 6H), 1.35 (t, J=7.1 Hz, 3H)

[Example 22] Preparation of 3,3-dimethyl-2-oxo-2-ethoxy-6-methyl-1,2-benzoxaphosphole

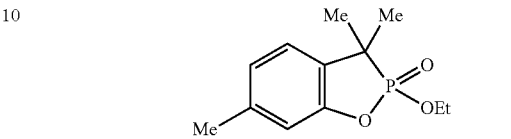

A reaction was performed by the same method as in Example 17 except for using 4-(methyl)-dimethylbenzylphosphonic acid monoethyl ester (48.5 mg, 0.2 mmol) instead of dimethylbenzylphosphonic acid monoethyl ester of Example 17, thereby obtaining 3,3-dimethyl-2-oxo-2-ethoxy-6-methyl-1,2-benzoxaphosphole (40.4 mg, 84%) corresponding to the target compound.

$^1$H NMR (400 MHz, CDCl$_3$) δ 7.04 (dd, J=7.7, 1.2 Hz, 1H), 6.91-6.88 (m, 1H), 6.82 (s, 1H), 4.34-4.24 (m, 2H), 2.33 (s, 3H), 1.50 (dd, J=17.6, 4.0 Hz, 6H), 1.35 (t, J=7.1 Hz, 3H)

[Example 23] Preparation of 3,3-dimethyl-2-oxo-2-ethoxy-6-tert-butyl-1,2-benzoxaphosphole

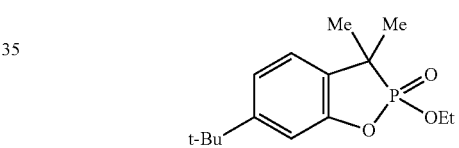

A reaction was performed by the same method as in Example 17 except for using 4-(t-butyl)-dimethylbenzylphosphonic acid monoethyl ester (56.9 mg, 0.2 mmol) instead of dimethylbenzylphosphonic acid monoethyl ester of Example 17, thereby obtaining 3,3-dimethyl-2-oxo-2-ethoxy-6-tert-butyl-1,2-benzoxaphosphole (46.9 mg, 83%) corresponding to the target compound.

$^1$H NMR (400 MHz, CDCl$_3$) δ 7.12-7.07 (m, 2H), 7.03 (m, 1H), 4.35-4.26 (m, 2H), 1.50 (dd, J=17.6, 2.8 Hz, 6H), 1.37 (t, J=7.1 Hz, 3H), 1.30 (s, 9H)

[Example 24] Preparation of 3,3-dimethyl-2-oxo-2-ethoxy-5-methoxy-1,2-benzoxaphosphole

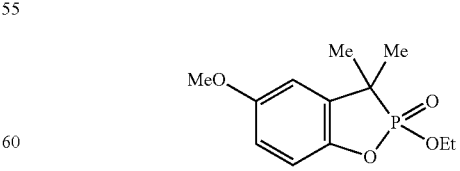

A reaction was performed by the same method as in Example 17 except for using 3-(methoxy)-dimethylbenzylphosphonic acid monoethyl ester (51.7 mg, 0.2 mmol) instead of dimethylbenzylphosphonic acid monoethyl ester of Example 17, thereby obtaining 3,3-dimethyl-2-oxo-2- ethoxy-5-methoxy-1,2-benzoxaphosphole (34.9 mg, 68%) corresponding to the target compound.

¹H NMR (400 MHz, CDCl₃) δ 6.93 (d, J=8.4 Hz, 1H), 6.76-6.72 (m, 2H), 4.34-4.24 (m, 2H), 3.78 (s, 3H), 1.51 (dd, J=17.5, 1.5 Hz, 6H), 1.35 (t, J=7.1 Hz, 3H)

[Example 25] Preparation of 3,3-dimethyl-2-oxo-2-ethoxy-6-methoxy-1,2-benzoxaphosphole

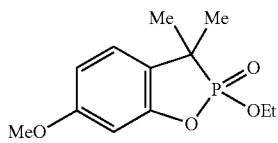 [SMILES: CCOP1(=O)Oc2cc(OC)ccc2C1(C)C]

A reaction was performed by the same method as in Example 17 except for using 4-(methoxy)-dimethylbenzylphosphonic acid monoethyl ester (51.7 mg, 0.2 mmol) instead of dimethylbenzylphosphonic acid monoethyl ester of Example 17, thereby obtaining 3,3-dimethyl-2-oxo-2-ethoxy-6-methoxy-1,2-benzoxaphosphole (35.9 mg, 70%) corresponding to the target compound.

¹H NMR (400 MHz, CDCl₃) δ 7.05 (dd, J=8.4 Hz, 1.4 Hz, 1H), 6.63 (ddd, J=8.5, 2.5, 0.9 Hz, 1H), 6.58 (dd, J=2.4 Hz, 0.9 Hz, 1H), 4.35-4.25 (m, 2H), 3.78 (s, 3H), 1.49 (dd, J=17.7, 2.7 Hz, 6H), 1.36 (t, J=7.1 Hz, 3H)

[Example 26] Preparation of 3,3-dimethyl-2-oxo-2-ethoxy-6-chloro-1,2-benzoxaphosphole

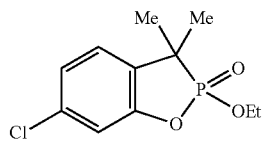 [SMILES: CCOP1(=O)Oc2cc(Cl)ccc2C1(C)C]

A reaction was performed by the same method as in Example 17 except for using 4-(chloro)-dimethylbenzylphosphonic acid monoethyl ester (52.5 mg, 0.2 mmol) instead of dimethylbenzylphosphonic acid monoethyl ester of Example 17, thereby obtaining 3,3-dimethyl-2-oxo-2-ethoxy-6-chloro-1,2-benzoxaphosphole (32.8 mg, 63%) corresponding to the target compound.

¹H NMR (400 MHz, CDCl₃) δ 7.11-7.06 (m, 2H), 7.03-7.03 (m, 1H), 4.36-4.26 (m, 2H), 1.50 (dd, J=17.6, 2.8 Hz, 6H), 1.37 (t, J=7.1 Hz, 3H)

[Example 27] Preparation of 3,3-dimethyl-2-oxo-2-ethoxy-6-trifluoromethyl-1,2-benzoxaphosphole

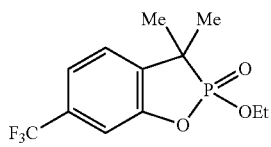 [SMILES: CCOP1(=O)Oc2cc(C(F)(F)F)ccc2C1(C)C]

A reaction was performed by the same method as in Example 17 except for using 4-(trifluoromethyl)-dimethylbenzylphosphonic acid monoethyl ester (59.3 mg, 0.2 mmol) instead of dimethylbenzylphosphonic acid monoethyl ester of Example 17, thereby obtaining 3,3-dimethyl-2-oxo-2-ethoxy-6-trifluoromethyl-1,2-benzoxaphosphole (36.5 mg, 62%) corresponding to the target compound.

¹H NMR (400 MHz, CDCl₃) δ 7.38-7.36 (m, 1H), 7.30-7.28 (m, 1H), 7.26 (s, 1H), 4.40-4.29 (m, 2H), 1.54 (dd, J=17.5, 4.9 Hz, 6H), 1.38 (t, J=7.1 Hz, 3H)

[Example 28] Preparation of 3,3-dipropyl-2-oxo-2-ethoxy-6-trifluoromethyl-1,2-benzoxaphosphole

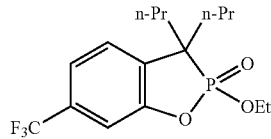

A reaction was performed by the same method as in Example 17 except for using 4-(trifluoromethyl)-dipropylbenzylphosphonic acid monoethyl ester (70.5 mg, 0.2 mmol) instead of dimethylbenzylphosphonic acid monoethyl ester of Example 17, thereby obtaining 3,3-dipropyl-2-oxo-2-ethoxy-6-trifluoromethyl-1,2-benzoxaphosphole (48.5 mg, 65%) corresponding to the target compound.

¹H NMR (400 MHz, CDCl₃) δ 7.35-7.33 (m, 1H), 7.26-7.23 (m, 2H), 4.38-4.24 (m, 2H), 2.02-1.57 (m, 5H), 1.46-1.37 (m, 2H), 1.36 (t, J=7.1 Hz, 3H), 1.20-1.10 (m, 1H), 0.98 (t, J=7.2 Hz, 3H), 0.88 (t, J=7.3 Hz, 3H)

[Example 29] Preparation of 3-cyclopentyl-2-oxo-2-ethoxy-1,2-benzoxaphosphole

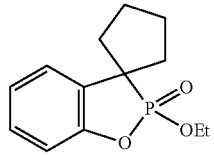 [SMILES: CCOP1(=O)Oc2ccccc2C12CCCC2]

A reaction was performed by the same method as in Example 17 except for using 1-phenylcyclopentylphosphonic acid ethyl ester (50.9 mg, 0.2 mmol) instead of dimethylbenzylphosphonic acid monoethyl ester of Example 17, thereby obtaining 3-cyclopentyl-2-oxo-2-ethoxy-1,2-benzoxaphosphole (40.4 mg, 80%) corresponding to a target compound.

¹H NMR (400 MHz, CDCl₃) δ 7.21-7.15 (m, 2H), 7.08-7.04 (m, 1H), 6.98-6.96 (m, 1H), 4.34-4.24 (m, 2H), 2.71-2.60 (m, 1H), 2.46-2.37 (m, 1H), 2.04-1.82 (m, 5H), 1.79-1.66 (m, 1H), 1.36 (t, J=7.1 Hz, 3H)

[Example 30] Preparation of 3-cyclohexyl-2-oxo-2-ethoxy-1,2-benzoxaphosphole

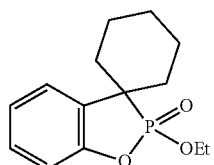

A reaction was performed by the same method as in Example 17 except for using 1-phenylcyclohexylphosphonic acid ethyl ester (53.8 mg, 0.2 mmol) instead of dimethylbenzylphosphonic acid monoethyl ester of Example 17, thereby obtaining 3-cyclohexyl-2-oxo-2-ethoxy-1,2-benzoxaphosphole (45.3 mg, 85%) corresponding to a target compound.

¹H NMR (400 MHz, CDCl₃) δ 7.22-7.15 (m, 2H), 7.08-7.04 (m, 1H), 6.98-6.96 (m, 1H), 4.37-4.27 (m, 2H), 2.25-2.17 (m, 1H), 2.15-2.09 (m, 1H), 2.07-2.00 (m, 1H), 1.90-1.80 (m, 2H), 1.78-1.71 (m, 2H), 1.64-1.45 (m, 2H), 1.39-1.29 (m, 1H), 1.36 (t, J=7.1 Hz, 3H)

[Example 31] Preparation of 3-ethyl-3-methyl-2-oxo-2-ethoxy-1,2-benzoxaphosphole

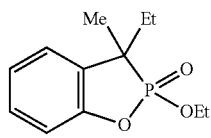 [SMILES: CCOP1(=O)Oc2ccccc2C1(C)CC]

A reaction was performed by the same method as in Example 17 except for using ethylmethylbenzylphosphonic acid monoethyl ester (48.5 mg, 0.2 mmol) instead of dimethylbenzylphosphonic acid monoethyl ester of Example 17, thereby obtaining 3-ethyl-3-methyl-2-oxo-2-ethoxy-1,2-benzoxaphosphole (40.4 mg, 84%, diastereomeric ratio=2:1) corresponding to the target compound.

¹H NMR (400 MHz, CDCl₃) data for the major isomer; δ 7.25-7.19 (m, 1H), 7.15-7.11 (m, 1H), 7.10-7.05 (m, 1H), 7.01-6.99 (m, 1H), 4.36-4.23 (m, 2H), 1.98-1.79 (m, 2H), 1.50 (d, J=17.8 Hz, 3H), 1.37 (t, J=7.1 Hz, 3H), 1.10 (t, J=7.5 Hz, 3H); data for the minor isomer; δ 7.25-7.19 (m, 1H), 7.15-7.11 (m, 1H), 7.10-7.05 (m, 1H), 7.01-6.99 (m, 1H), 4.36-4.23 (m, 2H), 1.98-1.79 (m, 2H), 1.50 (d, J=17.8 Hz, 3H), 1.34 (t, J=7.1, 3H), 0.96 (t, J=7.4 Hz, 3H);

[Example 32] Preparation of 3,3-dimethyl-2-oxo-2-ethoxy-6-phenyl-1,2-benzoxaphosphole

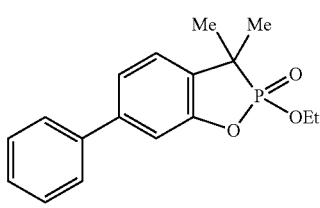 [SMILES: CCOP1(=O)Oc2cc(-c3ccccc3)ccc2C1(C)C]

A reaction was performed by the same method as in Example 17 except for using 4-(phenyl)-dimethylbenzylphosphonic acid monoethyl ester (60.9 mg, 0.2 mmol) instead of dimethylbenzylphosphonic acid monoethyl ester of Example 17, thereby obtaining 3,3-dimethyl-2-oxo-2-ethoxy-6-phenyl-1,2-benzoxaphosphole (45.9 mg, 76%) corresponding to the target compound.

¹H NMR (400 MHz, CDCl₃) δ 8.98 (s, 1H), 7.58-7.52 (m, 6H), 7.41 (t, J=7.5 Hz, 2H), 7.33-7.30 (m, 1H), 3.81-3.78 (m, 2H), 1.60 (d, J=15.8 Hz, 6H), 1.11 (t, J=6.9 Hz, 3H)

[Example 33] Preparation of 3,3-dimethyl-2-oxo-2-ethoxy-6-(3-methyl)phenyl-1,2-benzoxaphosphole

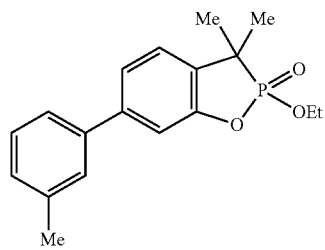 [SMILES: CCOP1(=O)Oc2cc(-c3cccc(C)c3)ccc2C1(C)C]

A reaction was performed by the same method as in Example 17 except for using 4-(3-methylphenyl)-dimethylbenzylphosphonic acid monoethyl ester (63.7 mg, 0.2 mmol) instead of dimethylbenzylphosphonic acid monoethyl ester of Example 17, thereby obtaining 3,3-dimethyl-2-oxo-2-ethoxy-6-(3-methyl)phenyl-1,2-benzoxaphosphole (43.0 mg, 68%) corresponding to the target compound.

¹H NMR (400 MHz, CDCl₃) δ 7.78 (s, 1H), 7.57-7.52 (m, 4H), 7.41-7.36 (m, 2H), 7.32-7.29 (m, 1H), 7.15-7.13 (m, 1H), 3.81-3.72 (m, 2H), 2.40 (s, 3H), 1.59 (d, J=16.8 Hz, 6H), 1.10 (t, J=7.1 Hz, 3H)

[Example 34] Preparation of 3,3-dimethyl-2-oxo-2-ethoxy-6-(4-methyl)phenyl-1,2-benzoxaphosphole

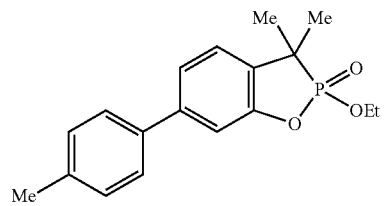 [SMILES: CCOP1(=O)Oc2cc(-c3ccc(C)cc3)ccc2C1(C)C]

A reaction was performed by the same method as in Example 17 except for using 4-(4-methylphenyl)-dimethylbenzylphosphonic acid monoethyl ester (63.7 mg, 0.2 mmol) instead of dimethylbenzylphosphonic acid monoethyl ester of Example 17, thereby obtaining 3,3-dimethyl-2-oxo-2-ethoxy-6-(4-methyl)phenyl-1,2-benzoxaphosphole (44.9 mg, 71%) corresponding to the target compound.

¹H NMR (400 MHz, CDCl₃) δ 7.45-7.43 (m, 2H), 7.30-7.28 (m, 1H), 7.25 (s, 1H), 7.23-7.20 (m, 3H), 4.37-4.28 (m, 2H), 2.39 (s, 3H), 1.55 (dd, J=17.6, 2.6 Hz, 6H), 1.37 (t, J=7.1 Hz, 3H)

[Example 35] Preparation of 3,3-dimethyl-2-oxo-2-ethoxy-6-(4-tert-butyl)phenyl-1,2-benzoxaphosphole

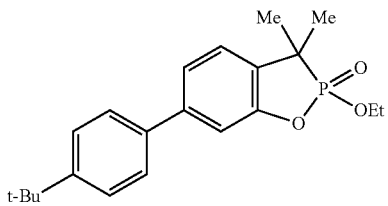

A reaction was performed by the same method as in Example 17 except for using 4-(4-t-butylphenyl)-dimethylbenzylphosphonic acid monoethyl ester (72.1 mg, 0.2 mmol) instead of dimethylbenzylphosphonic acid monoethyl ester of Example 17, thereby obtaining 3,3-dimethyl-2-oxo-2-ethoxy-6-(4-tert-butyl)phenyl-1,2-benzoxaphosphole (53.0 mg, 74%) corresponding to the target compound.

$^1$H NMR (400 MHz, CDCl$_3$) δ 7.50-7.45 (m, 4H), 7.32-7.30 (m, 1H), 7.22-7.20 (m, 2H), 4.39-4.28 (m, 2H), 1.55 (dd, J=17.6, 2.1 Hz, 6H), 1.37 (t, J=7.0 Hz, 3H), 1.35 (s, 9H)

[Example 36] Preparation of 3,3-dimethyl-2-oxo-2-ethoxy-6-(3-methoxy)phenyl-1,2-benzoxaphosphole

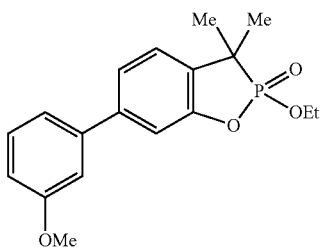

A reaction was performed by the same method as in Example 17 except for using 4-(3-methoxyphenyl)-dimethylbenzylphosphonic acid monoethyl ester (66.9 mg, 0.2 mmol) instead of dimethylbenzylphosphonic acid monoethyl ester of Example 17, thereby obtaining 3,3-dimethyl-2-oxo-2-ethoxy-6-(3-methoxy)phenyl-1,2-benzoxaphosphole (47.9 mg, 72%) corresponding to the target compound.

$^1$H NMR (400 MHz, CDCl$_3$) δ 7.35 (t, J=7.9 Hz, 1H), 7.33-7.30 (m, 1H), 7.24-7.22 (m, 2H), 7.14-7.12 (m, 1H), 7.07-7.07 (m, 1H), 6.91 (ddd, J=8.2, 2.6, 0.9 Hz, 1H), 4.38-4.28 (m, 2H), 3.86 (s, 3H), 1.55 (dd, J=17.6, 2.6 Hz, 6H), 1.38 (t, J=7.1 Hz, 3H)

[Example 37] Preparation of 3,3-dimethyl-2-oxo-2-ethoxy-6-(4-methoxy)phenyl-1,2-benzoxaphosphole

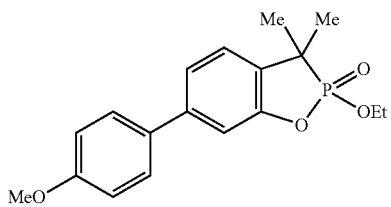 [SMILES: CCOP1(=O)Oc2cc(-c3ccc(C(C)(C)C)cc3)ccc2C1(C)C]

A reaction was performed by the same method as in Example 17 except for using 4-(4-methoxyphenyl)-dimethylbenzylphosphonic acid monoethyl ester (66.9 mg, 0.2 mmol) instead of dimethylbenzylphosphonic acid monoethyl ester of Example 17, thereby obtaining 3,3-dimethyl-2-oxo-2-ethoxy-6-(4-methoxy)phenyl-1,2-benzoxaphosphole (36.6 mg, 55%) corresponding to the target compound.

$^1$H NMR (400 MHz, CDCl$_3$) δ 7.50-7.47 (m, 2H), 7.28-7.26 (m, 1H), 7.21-7.19 (m, 2H), 6.99-6.95 (m, 2H), 4.37-4.28 (m, 2H), 3.85 (s, 3H), 1.55 (dd, J=17.6, 2.4 Hz, 6H), 1.38 (t, J=7.1 Hz, 3H)

[Example 38] Preparation of 3,3-dimethyl-2-oxo-2-ethoxy-6-(4-chloro)phenyl-1,2-benzoxaphosphole

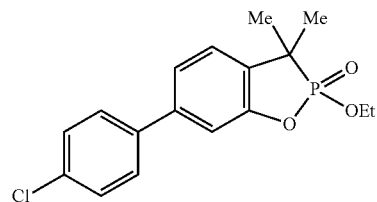 [SMILES: CCOP1(=O)Oc2cc(-c3ccc(Cl)cc3)ccc2C1(C)C]

A reaction was performed by the same method as in Example 17 except for using 4-(4-chlorophenyl)-dimethylbenzylphosphonic acid monoethyl ester (67.8 mg, 0.2 mmol) instead of dimethylbenzylphosphonic acid monoethyl ester of Example 17, thereby obtaining 3,3-dimethyl-2-oxo-2-ethoxy-6-(4-chloro)phenyl-1,2-benzoxaphosphole (49.8 mg, 74%) corresponding to the target compound.

$^1$H NMR (400 MHz, CDCl$_3$) δ 7.57-7.49 (m, 6H), 7.40-7.37 (m, 2H), 6.84 (s, 1H), 3.82-3.75 (m, 2H), 1.59 (d, J=16.8 Hz, 6H), 1.11 (t, J=7.1 Hz, 3H)

[Example 39] Preparation of 3,3-dimethyl-2-oxo-2-ethoxy-6-(3,5-dimethyl) phenyl-1,2-benzoxaphosphole

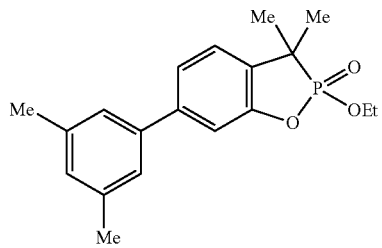 [SMILES: CCOP1(=O)Oc2cc(-c3cc(C)cc(C)c3)ccc2C1(C)C]

A reaction was performed by the same method as in Example 17 except for using 4-(3,5-dimethylphenyl)-dimethylbenzylphosphonic acid monoethyl ester (66.5 mg, 0.2 mmol) instead of dimethylbenzylphosphonic acid monoethyl ester of Example 17, thereby obtaining 3,3-dimethyl-2-oxo-2-ethoxy-6-(3,5-dimethyl) phenyl-1,2-benzoxaphosphole (44.9 mg, 68%) corresponding to the target compound.

$^1$H NMR (400 MHz, CDCl$_3$) δ 7.30-7.28 (m, 1H), 7.21-7.19 (m, 1H), 7.15 (s, 2H), 7.00 (s, 1H), 4.37-4.28 (m, 2H), 2.37 (s, 6H), 1.55 (dd, J=17.6, 2.6 Hz, 6H), 1.37 (t, J=7.1 Hz, 3H)

[Example 40] Preparation of 6-ethoxy-6H-dibenz[c,e]oxaphosphorin-6-oxide

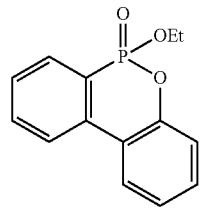 [SMILES: CCOP1(=O)Oc2ccccc2-c2ccccc21]

After Pd(OAc)$_2$ (4.5 mg, 0.02 mmol), PhI(OAc)$_2$ (128.8 mg, 0.4 mmol), KOAc (39.3 mg, 0.4 mmol), N-acetyl-L-leucine (10.4 mg, 0.06 mmol), 1,1'-biphenylphosphonic acid monomethyl ester (52.4 mg, 0.2 mmol), and t-BuOH (2.5 mL) were put into a V-vial, the V-vial was covered with a cap and the mixture was stirred and heated at 100° C. for 12 hours. After the reactant was extracted with dichloromethane, filtered using celite, and dried over MgSO$_4$, the solvent was concentrated and removed, and the resultant was separated using column chromatography (ethyl acetate: hexane=1:1), thereby obtaining 6-ethoxy-6H-dibenz[c,e] oxaphosphorin-6-oxide (28.9 mg, 0.111 mmol, 55%).

$^1$H NMR (400 MHz, CDCl$_3$, 25° C., TMS): =8.00-7.93 (m, 3H), 7.74-7.70 (m, 1H), 7.55-7.50 (m, 1H), 7.41-7.37 (m, 1H), 4.26-4.19 (m, 2H), 1.28 (t, J=7.1 Hz, 3H)

[Example 41] Preparation of 6-ethoxy-1-methyl-6H-dibenz[c,e]oxaphosphorin-6-oxide

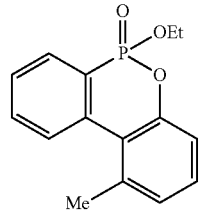 [SMILES: CCOP1(=O)Oc2cccc(C)c2-c2ccccc21]

A reaction was performed by the same method as in Example 40 except for using 2'-methyl-1,1'-biphenylphosphonic acid monoethyl ester (55.2 mg, 0.2 mmol) instead of 1,1'-biphenylphosphonic acid monoethyl ester of Example 40, thereby obtaining 6-ethoxy-1-methyl-6H-dibenz[c,e] oxaphosphorin-6-oxide (28.9 mg, 0.111 mmol, 55%) corresponding to the target compound.

$^1$H NMR (400 MHz, CDCl$_3$)=8.01 (ddd, J=15.0, 7.5, 1.1 Hz, 1H), 7.84 (t, J=7.2 Hz, 3H), 7.70-7.66 (m, 1H), 7.52-7.48 (m, 1H), 7.28-7.24 (m, 1H), 7.12 (d, J=17.9 Hz, 1H), 4.29-4.14 (m, 2H), 2.70 (s, 3H), 1.25 (t, J=7.1 Hz, 3H)

[Example 42] Preparation of 6-ethoxy-2-methyl-6H-dibenz[c,e]oxaphosphorin-6-oxide

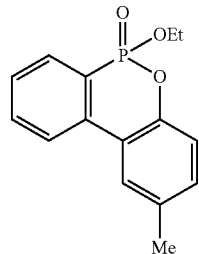 [SMILES: CCOP1(=O)Oc2ccc(C)cc2-c2ccccc21]

A reaction was performed by the same method as in Example 40 except for using 3'-methyl-1,1'-biphenylphosphonic acid monoethyl ester (55.2 mg, 0.2 mmol) instead of 1,1'-biphenylphosphonic acid monoethyl ester of Example 40, thereby obtaining 6-ethoxy-2-methyl-6H-dibenz[c,e] oxaphosphorin-6-oxide (28.9 mg, 0.111 mmol, 55%) corresponding to the target compound.

$^1$H NMR (400 MHz, CDCl$_3$)=8.00-7.93 (m, 2H), 7.72-7.68 (m, 2H), 7.52-7.48 (m, 1H), 7.18 (d, J=8.3 Hz, 1H), 7.12 (d, J=8.3 Hz, 1H), 4.24-4.17 (m, 2H), 2.41 (s, 3H), 1.27 (t, J=7.1 Hz, 3H)

[Example 43] Preparation of 6-ethoxy-3-methyl-6H-dibenz[c,e]oxaphosphorin-6-oxide

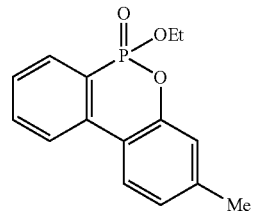 [SMILES: CCOP1(=O)Oc2cc(C)ccc2-c2ccccc21]

A reaction was performed by the same method as in Example 40 except for using 4'-methyl-1,1'-biphenylphosphonic acid monoethyl ester (55.2 mg, 0.2 mmol) instead of 1 r-biphenylphosphonic acid monoethyl ester of Example 40, thereby obtaining 6-ethoxy-3-methyl-6H-dibenz[c,e] oxaphosphorin-6-oxide (28.9 mg, 0.111 mmol, 55%) corresponding to the target compound.

$^1$H NMR (400 MHz, CDCl$_3$) δ 8.00-7.91 (m, 2H), 7.81 (d, J=8.1 Hz, 1H), 7.70 (t, J=7.8 Hz, 1H), 7.50-7.46 (m, 1H), 7.08 (d, J=8.2 Hz, 1H), 7.05 (s, 1H), 4.25-4.17 (m, 2H), 2.40 (s, 3H), 1.28 (t, J=7.1 Hz, 3H)

[Example 44] Preparation of 6-ethoxy-3-tert-butyl-6H-dibenz[c,e]oxaphosphorin-6-oxide

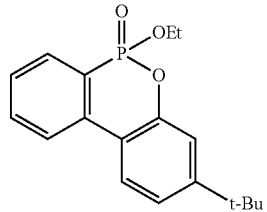 [SMILES: CCOP1(=O)Oc2cc(C(C)(C)C)ccc2-c2ccccc21]

A reaction was performed by the same method as in Example 40 except for using 4'-t-butyl-1,1'-biphenylphosphonic acid monoethyl ester (63.6 mg, 0.2 mmol) instead of 1,1'-' biphenylphosphonic acid monoethyl ester of Example 40, thereby obtaining 6-ethoxy-3-tert-butyl-6H-dibenz[c,e] oxaphosphorin-6-oxide (28.9 mg, 0.111 mmol, 55%) corresponding to the target compound.

$^1$H NMR (400 MHz, CDCl$_3$) δ 7.97-7.92 (m, 2H), 7.85 (d, J=8.4 Hz, 1H), 7.72-7.67 (m, 1H), 7.51-7.46 (m, 1H), 7.29 (dd, J=8.4, 1.8 Hz, 1H), 7.23 (d, J=2.0 Hz, 1H), 4.26-4.19 (m, 2H), 1.35 (s, 9H), 1.29 (t, J=7.1 Hz, 3H)

[Example 45] Preparation of 6-ethoxy-3-methoxy-6H-dibenz[c,e]oxaphosphorin-6-oxide

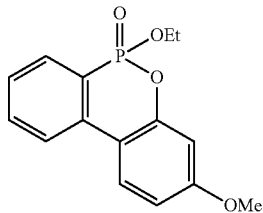 [SMILES: CCOP1(=O)Oc2cc(OC)ccc2-c2ccccc21]

A reaction was performed by the same method as in Example 40 except for using 4'-methoxy-1,1'-biphenylphosphonic acid monoethyl ester (58.4 mg, 0.2 mmol) instead of 1,1'-biphenylphosphonic acid monoethyl ester of Example 40, thereby obtaining 6-ethoxy-3-methoxy-6H-dibenz[c,e]oxaphosphorin-6-oxide (28.9 mg, 0.111 mmol, 55%) corresponding to the target compound.

$^1$H NMR (400 MHz, CDCl$_3$) δ 7.95 (ddd, J=14.6, 7.6, 1.1 Hz, 1H), 7.89-7.82 (m, 2H), 7.70-7.66 (m, 1H), 7.47-7.43 (m, 1H), 6.84 (dd, J=8.8, 2.6 Hz, 1H), 6.76 (d, J=2.6 Hz, 1H), 4.26-4.18 (m, 2H), 3.87 (s, 3H), 1.29 (t, J=7.1 Hz, 3H)

[Example 46] Preparation of 5-ethoxy-2,3-dimethoxy-6H-dibenz[c,e]oxaphosphorin-5-oxide

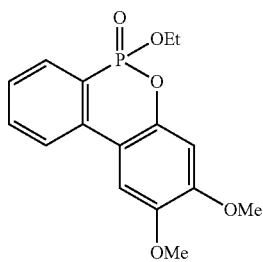 [SMILES: CCOP1(=O)Oc2cc(OC)c(OC)cc2-c2ccccc21]

A reaction was performed by the same method as in Example 40 except for using 3',4'-dimethoxy-1,1'-biphenylphosphonic acid monoethyl ester (64.4 mg, 0.2 mmol) instead of 1,1'-biphenylphosphonic acid monoethyl ester of Example 40, thereby obtaining 5-ethoxy-2,3-dimethoxy-6H-dibenz[c,e]oxaphosphorin-5-oxide (28.9 mg, 0.111 mmol, 55%) corresponding to the target compound.

$^1$H NMR (400 MHz, CDCl$_3$) δ 7.95 (ddd, J=14.6, 7.5, 1.0 Hz, 1H), 7.83 (t, J=7.2 Hz, 1H), 7.69 (t, J=7.8 Hz, 1H), 7.48-7.43 (m, 1H), 7.32 (s, 1H), 4.25-4.18 (m, 2H), 3.95 (d, J=14.5 Hz, 6H), 1.29 (t, J=7.1 Hz, 3H)

[Example 47] Preparation of 6-ethoxy-3-phenyl-6H-dibenz[c,e]oxaphosphorin-6-oxide

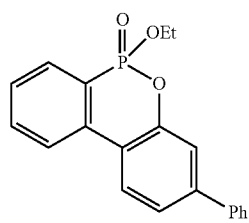 [SMILES: CCOP1(=O)Oc2cc(-c3ccccc3)ccc2-c2ccccc21]

A reaction was performed by the same method as in Example 40 except for using 4'-phenyl-1,1'-biphenylphosphonic acid monoethyl ester (67.6 mg, 0.2 mmol) instead of 1 r-biphenylphosphonic acid monoethyl ester of Example 40, thereby obtaining 6-ethoxy-3-phenyl-6H-dibenz[c,e]oxaphosphorin-6-oxide (28.9 mg, 0.111 mmol, 55%) corresponding to the target compound.

$^1$H NMR (400 MHz, CDCl$_3$) δ 8.02 (m, 3H), 7.75-7.71 (m, 1H), 7.66-7.63 (m, 2H), 7.55-7.46 (m, 5H), 7.43-7.39 (m, 1H), 4.29-4.21 (m, 2H), 1.30 (t, J=7.1 Hz, 3H)

[Example 48] Preparation of 5-ethoxy-5H-benzo[c]naphtho[2,3-e][1,2]oxaphosphorin-5-oxide

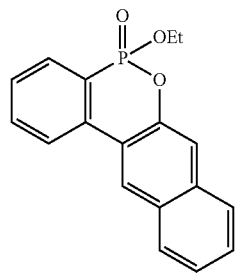 [SMILES: CCOP1(=O)Oc2cc3ccccc3cc2-c2ccccc21]

A reaction was performed by the same method as in Example 40 except for using 2-(naphthalene-2-yl)phenylphosphonic acid monoethyl ester (62.4 mg, 0.2 mmol) instead of L biphenylphosphonic acid monoethyl ester of Example 40, thereby obtaining 5-ethoxy-5H-benzo[c]naphtho[2,3-e][1,2]oxaphosphorin-5-oxide (28.9 mg, 0.111 mmol, 55%) corresponding to the target compound.

$^1$H NMR (400 MHz, CDCl$_3$) δ 8.40 (s, 1H), 8.13 (t, J=7.2 Hz, 1H), 8.02 (ddd, J=14.6, 7.5, 1.0 Hz, 1H), 7.90 (d, J=8.1 Hz, 1H), 7.80 (d, J=8.1 Hz, 1H), 7.76-7.73 (m, 1H), 4.28-4.20 (m, 2H), 1.26 (t, J=7.1 Hz, 3H)

[Example 49] Preparation of 5-ethoxy-5H-benzo[c]naphtho[1,2-e][1,2]oxaphosphorin-5-oxide

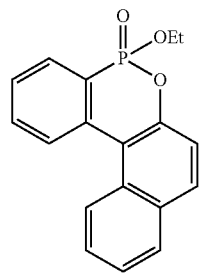 [SMILES: CCOP1(=O)Oc2ccc3ccccc3c2-c2ccccc21]

A reaction was performed by the same method as in Example 40 except for using 2-(naphthalene-1-yl)phenylphosphonic acid monoethyl ester (62.4 mg, 0.2 mmol) instead of 1,1'-biphenylphosphonic acid monoethyl ester of Example 40, thereby obtaining 5-ethoxy-5H-benzo[c]naphtho[1,2-e][1,2]oxaphosphorin-5-oxide (28.9 mg, 0.111 mmol, 55%) corresponding to the target compound.

¹H NMR (400 MHz, CDCl₃) δ 8.52 (d, J=8.5 Hz, 1H), 8.17 (t, J=7.0 Hz, 1H), 8.08 (ddd, J=14.8, 7.5, 0.8 Hz, 1H), 7.90 (dd, J=14.3, 8.0 Hz, 2H), 7.74 (t, J=7.8 Hz, 1H), 7.60-7.49 (m, 3H), 7.38 (d, J=8.8 Hz, 1H), 4.30-4.15 (m, 2H), 1.22 (t, J=7.1 Hz, 3H)

[Example 50] Preparation of 6-ethoxy-1-fluoro-6H-dibenz[c,e]oxaphosphorin-6-oxide

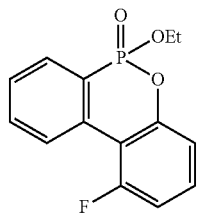 [SMILES: CCOP1(=O)Oc2cccc(F)c2-c2ccccc21]

A reaction was performed by the same method as in Example 40 except for using 2'-fluoro-1,1'-biphenylphosphonic acid monoethyl ester (56.0 mg, 0.2 mmol) instead of 1,1'-biphenylphosphonic acid monoethyl ester of Example 40, thereby obtaining 6-ethoxy-1-fluoro-6H-dibenz[c,e]oxaphosphorin-6-oxide (28.9 mg, 0.111 mmol, 55%) corresponding to the target compound.

¹H NMR (400 MHz, CDCl₃) δ 8.27 (t, J=7.3 Hz, 1H), 8.04-8.00 (m, 1H), 7.72 (t, J=7.8 Hz, 1H), 7.57-7.52 (m, 1H), 7.09-7.01 (m, 2H), 4.28-4.20 (m, 2H), 1.28 (t, J=7.1 Hz, 3H)

[Example 51] Preparation of 6-ethoxy-2-chloro-6H-dibenz[c,e]oxaphosphorin-6-oxide

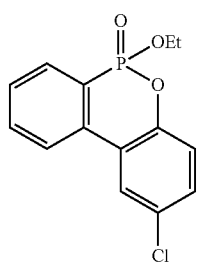 [SMILES: CCOP1(=O)Oc2ccc(Cl)cc2-c2ccccc21]

A reaction was performed by the same method as in Example 40 except for using 3'-chloro-1,1'-biphenylphosphonic acid monoethyl ester (59.2 mg, 0.2 mmol) instead of biphenylphosphonic acid monoethyl ester of Example 40, thereby obtaining 6-ethoxy-2-chloro-6H-dibenz[c,e]oxaphosphorin-6-oxide (28.9 mg, 0.111 mmol, 55%) corresponding to the target compound.

¹H NMR (400 MHz, CDCl₃) δ 8.00 (ddd, J=14.6, 7.6, 1.1 Hz, 1H), 7.94-7.90 (m, 2H), 7.76-7.72 (m, 1H), 7.59-7.52 (m, 1H), 7.36-7.33 (m, 1H), 7.19 (d, J=8.6 Hz, 1H), 4.27-4.20 (m, 2H), 1.29 (t, J=7.1 Hz, 3H)

[Example 52] Preparation of 6-ethoxy-3-chloro-6H-dibenz[c,e]oxaphosphorin-6-oxide

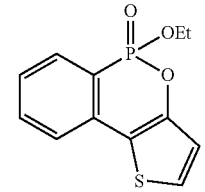 [SMILES: CCOP1(=O)Oc2ccsc2-c2ccccc21]

A reaction was performed by the same method as in Example 40 except for using 4'-chloro-1,1'-biphenylphosphonic acid monoethyl ester (59.2 mg, 0.2 mmol) instead of 1,1'-biphenyl phosphonic acid monoethyl ester of Example 40, thereby obtaining 6-ethoxy-3-chloro-6H-dibenz[c,e]oxaphosphorin-6-oxide (28.9 mg, 0.111 mmol, 55%) corresponding to the target compound.

¹H NMR (400 MHz, CDCl₃) δ 8.00 (ddd, J=14.7, 7.6, 1.0 Hz, 1H), 7.92 (t, J=7.2 Hz, 1H), 7.90 (d, J=9.1 Hz, 1H), 7.75-7.70 (m, 1H), 7.57-7.52 (m, 1H), 7.27-7.25 (m, 2H), 4.29-4.20 (m, 2H), 1.30 (t, J=7.1 Hz, 3H)

[Example 53] Preparation of 5-ethoxy-5H-benzo[c]thieno[2,3-e][1,2]oxaphosphorin-5-oxide

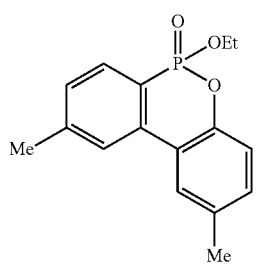

A reaction was performed by the same method as in Example 40 except for using 2-(thiophen-2-yl)phenylphosphonic acid monoethyl ester (53.6 mg, 0.2 mmol) instead of 1,1'-biphenylphosphonic acid monoethyl ester of Example 40, thereby obtaining 5-ethoxy-5-benzo[c]thieno[2,3-e][1,2]oxaphosphorin-5-oxide (28.9 mg, 0.111 mmol, 55%) corresponding to the target compound.

¹H NMR (400 MHz, CDCl₃) δ 7.92 (ddd, J=14.1, 7.6, 0.7 Hz, 1H), 7.64-7.60 (m, 1H), 7.51-7.47 (m, 1H), 7.44-7.39 (m, 1H), 7.26-7.25 (m, 1H), 4.27-4.19 (m, 2H), 1.32 (t, J=7.1 Hz, 3H)

[Example 54] Preparation of 6-ethoxy-2,9-dimethyl-6H-dibenz[c,e]oxaphosphorin-6-oxide A reaction was performed by the same method as in Example 40 except for using 3'-methyl-5-methyl-1,1'-biphenylphosphonic acid monoethyl ester (58.0 mg, 0.2 mmol) instead of 1,1'-biphenylphosphonic acid monoethyl ester of Example 40, thereby obtaining 6-ethoxy-2,9-dimethyl-6H-dibenz[c,e]oxaphosphorin-6-oxide (28.9 mg, 0.111 mmol, 55%) corresponding to the target compound.

$^1$H NMR (400 MHz, CDCl$_3$) δ 7.86 (dd, J=14.4, 7.7 Hz, 1H), 7.76 (d, J=6.0 Hz, 1H), 7.71 (d, J=1.5 Hz, 1H), 7.33-7.30 (m, 1H), 7.17 (d, J=8.3 Hz, 1H), 7.10 (d, J=8.2 Hz, 1H), 4.21-4.14 (m, 2H), 2.50 (s, 3H), 2.41 (s, 3H), 1.26 (t, J=7.1 Hz, 3H)

[Example 55] Preparation of 6-ethoxy-2,3-dimethoxy-9-methyl-6H-dibenz[c,e]oxaphosphorin-6-oxide

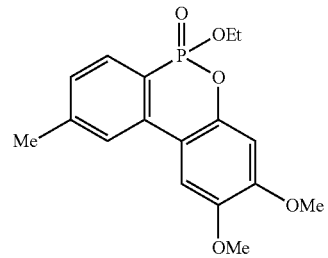 [SMILES: CCOP1(=O)Oc2cc(OC)c(OC)cc2-c2cc(C)ccc21]

A reaction was performed by the same method as in Example 40 except for using 3'-methyl-5-methyl-1,1'-biphenylphosphonic acid monoethyl ester (67.2 mg, 0.2 mmol) instead of 1,1'-biphenylphosphonic acid monoethyl ester of Example 40, thereby obtaining 6-ethoxy-2,3-dimethoxy-9-methyl-6H-dibenz[c,e]oxaphosphorin-6-oxide (28.9 mg, 0.111 mmol, 55%) corresponding to the target compound.

$^1$H NMR (400 MHz, CDCl$_3$) δ 7.83 (dd, J=14.4, 7.7 Hz, 1H), 7.61 (d, J=6.0 Hz, 1H), 7.31 (s, 1H), 7.28-7.26 (m, 1H), 6.74 (s, 1H), 4.23-4.15 (m, 2H), 3.99 (s, 3H), 3.93 (s, 3H), 2.50 (s, 3H), 1.28 (t, J=7.1 Hz, 3H)

[Example 56] Preparation of 6-ethoxy-2-chloro-9-methyl-6H-dibenz[c,e]oxaphosphorin-6-oxide

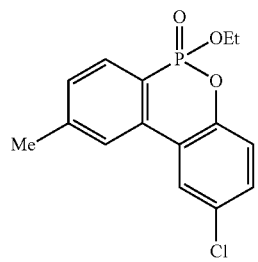 [SMILES: CCOP1(=O)Oc2ccc(Cl)cc2-c2cc(C)ccc21]

A reaction was performed by the same method as in Example 40 except for using 3'-chloro-5-methyl-1,1'-biphenylphosphonic acid monoethyl ester (62.0 mg, 0.2 mmol) instead of 1,1'-biphenylphosphonic acid monoethyl ester of Example 40, thereby obtaining 6-ethoxy-2-chloro-9-methyl-6H-dibenz[c,e]oxaphosphorin-6-oxide (28.9 mg, 0.111 mmol, 55%) corresponding to the target compound.

$^1$H NMR (400 MHz, CDCl$_3$) δ 7.90-7.84 (m, 2H), 7.71 (d, J=6.0 Hz, 1H), 7.39-7.36 (m, 1H), 7.17 (d, J=8.7 Hz, 1H), 4.25-4.17 (m, 2H), 2.51 (s, 3H), 1.28 (t, J=7.1 Hz, 3H)

[Example 57] Preparation of 6-ethoxy-2-methyl-8-fluoro-6H-dibenz[c,e]oxaphosphorin-6-oxide

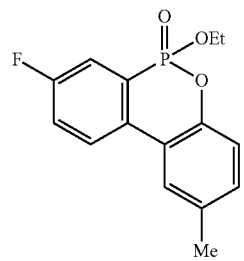 [SMILES: CCOP1(=O)Oc2ccc(C)cc2-c2ccc(F)cc21]

A reaction was performed by the same method as in Example 40 except for using 3'-methyl-1,1'-biphenyl-4-fluorophosphonic acid monoethyl ester (58.8 mg, 0.2 mmol) instead of 1,1'-biphenylphosphonic acid monoethyl ester of Example 40, thereby obtaining 6-ethoxy-2-methyl-8-fluoro-6H-dibenz[c,e]oxaphosphorin-6-oxide (28.9 mg, 0.111 mmol, 55%) corresponding to the target compound.

$^1$H NMR (400 MHz, CDCl$_3$) δ 7.98-7.92 (m, 1H), 7.68-7.61 (m, 2H), 7.38 (td, J=12.8, 2.8 Hz, 1H), 7.18 (d, J=8.3 Hz, 1H), 7.12 (d, J=8.3 Hz, 1H), 4.26-4.19 (m, 2H), 2.41 (s, 3H), 1.29 (t, J=7.1 Hz, 3H)

[Example 58] Preparation of 6-ethoxy-2,3-dimethoxy-8-fluoro-6H-dibenz[c,e]oxaphosphorin-6-oxide

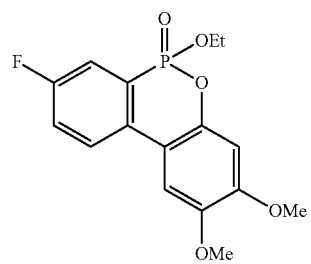 [SMILES: CCOP1(=O)Oc2cc(OC)c(OC)cc2-c2ccc(F)cc21]

A reaction was performed by the same method as in Example 40 except for using 3',4'-dimethoxy-4-fluoro-1,1'-biphenylphosphonic acid monoethyl ester (68.0 mg, 0.2 mmol) instead of 1,1'-biphenylphosphonic acid monoethyl ester of Example 40, thereby obtaining 6-ethoxy-2,3-dimethoxy-8-fluoro-6H-dibenz[c,e]oxaphosphorin-6-oxide (28.9 mg, 0.111 mmol, 55%) corresponding to the target compound.

$^1$H NMR (400 MHz, CDCl$_3$) δ 7.85-7.80 (m, 1H), 7.63 (ddd, J=15.7, 7.6, 2.7 Hz, 1H), 7.38 (td, J=12.8, 2.6 Hz, 1H), 7.26 (s, 1H), 6.75 (s, 1H), 4.28-4.20 (m, 2H), 4.00 (s, 3H), 3.93 (s, 3H), 1.31 (t, J=7.1 Hz, 3H)

[Example 59] Preparation of 6-ethoxy-2-chloro-8-fluoro-6H-dibenz[c,e]oxaphosphorin-6-oxide

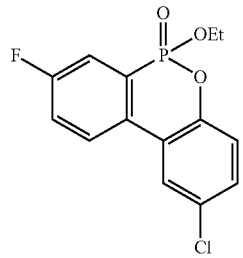 [SMILES: CCOP1(=O)Oc2ccc(Cl)cc2-c2ccc(F)cc21]

A reaction was performed by the same method as in Example 40 except for using 3'-chloro-4-fluoro-1,1'-biphenylphosphonic acid monoethyl ester (62.8 mg, 0.2 mmol) instead of 1,1'-biphenylphosphonic acid monoethyl ester of Example 40, thereby obtaining 6-ethoxy-2-chloro-8-fluoro-6H-dibenz[c,e]oxaphosphorin-6-oxide (28.9 mg, 0.111 mmol, 55%) corresponding to the target compound.

$^1$H NMR (400 MHz, CDCl$_3$) δ 7.94-7.89 (m, 1H), 7.84 (d, J=2.4 Hz, 1H), 7.68 (ddd, J=15.7, 10.2, 2.8 Hz, 1H), 7.42 (td, J=12.8, 2.8 Hz, 1H), 7.36-7.33 (m, 1H), 7.20 (d, J=8.7 Hz, 1H), 4.30-4.22 (m, 2H), 1.31 (t, J=7.1 Hz, 3H)

The cyclic phosphinate derivative according to the present invention may have pharmacological and physiological activities, be used as the basic skeleton of the natural material, and be used as the important raw material or intermediate capable of being used in development of a new drug, synthesis of various medicines, and the crop protection agent field.

In addition, with the method of preparing a cyclic phosphinate derivative according to the present invention, the cyclic phosphinate derivatives in which various substituents are introduced may be prepared with high yield through the simple synthetic process by performing the intramolecular carbon-oxygen coupling reaction on the phosphinic acid derivative in the presence of the palladium (Pd) catalyst, the oxidant, and the base.

What is claimed is:

1. A compound represented by the following Chemical Formula 3:

[Chemical Formula 3]

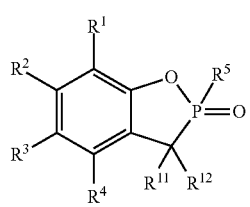

in Chemical Formula 3,
R$^1$ to R$^4$ are each independently hydrogen, (C1-C20)alkyl, halo(C1-C20)alkyl, (C1-C20)alkoxy, (C6-C20)aryl, halogen, (C6-C20)aryloxy, or tri(C1-C20)alkylsilyl;
R$^5$ is (C1-C20)alkyl, (C1-C20)alkoxy, or (C6-C20)aryl;
R$^{11}$ and R$^{12}$ are each independently (C1-C20)alkyl, or are linked to each other by (C1-C7)alkylene to form a spiro ring; and the alkyl and aryl of R$^1$ to R$^5$ are optionally substituted with a substituent selected from the group consisting of halogen, (C1-C20)alkyl, (C1-C20)alkoxy, and halo(C1-C20)alkyl.

2. The compound of claim 1, wherein R$^1$ to R$^4$ are each independently hydrogen, methyl, ethyl, propyl, butyl, pentyl, hexyl, trifluoromethyl, methoxy, ethoxy, propoxy, butoxy, pentyloxy, hexyloxy, phenyl, naphthyl, fluorenyl, chloro, bromo, fluoro, or trimethylsilyl (TMS), the phenyl, naphthyl, or fluorenyl of R$^1$ to R$^4$ are optionally substituted with a substituent selected from the group consisting of chloro, bromo, fluoro, methyl, ethyl, propyl, butyl, pentyl, hexyl, methoxy, ethoxy, propoxy, butoxy, pentyloxy, hexyloxy, and trifluoromethyl;
R$^5$ is methyl, ethyl, propyl, butyl, pentyl, hexyl, methoxy, ethoxy, propoxy, butoxy, pentyloxy, hexyloxy, phenyl, or naphthyl, the phenyl or naphthyl of R$^5$ are optionally substituted with a substituent selected from the group consisting of chloro, bromo, fluoro, methyl, ethyl, propyl, butyl, pentyl, hexyl, methoxy, ethoxy, propoxy, butoxy, pentyloxy, hexyloxy, and trifluoromethyl; and
R$^{11}$ and R$^{12}$ are each independently methyl, ethyl, propyl, butyl, pentyl, or hexyl, or are linked to each other by butylene or pentylene to form a spiro ring.

3. The compound of claim 2, wherein it is selected from the following compounds:

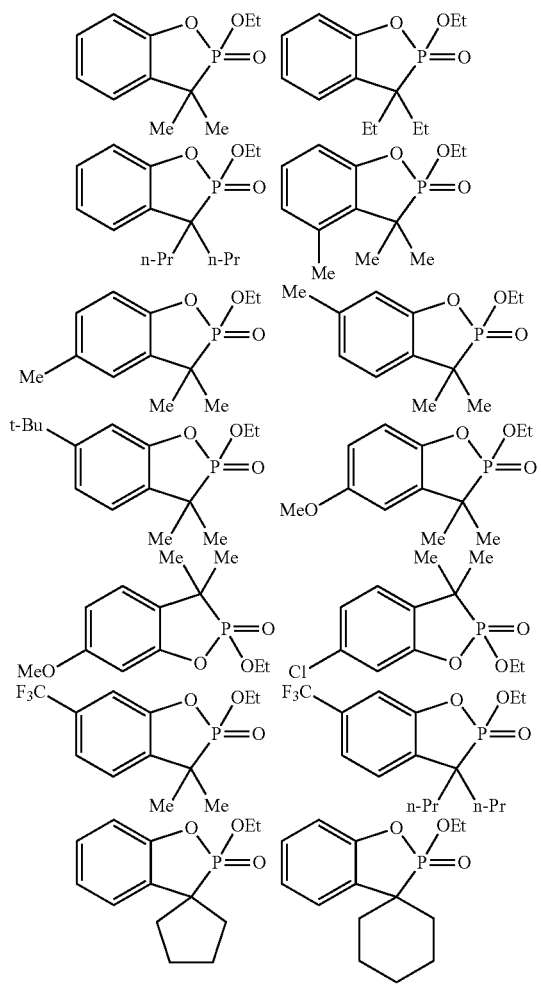

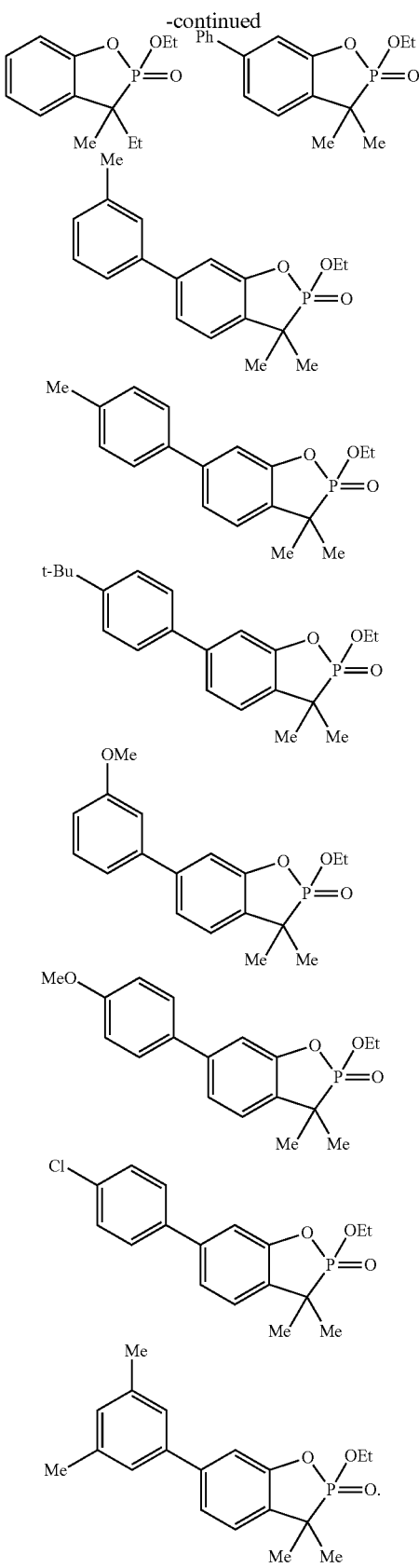
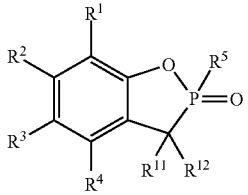
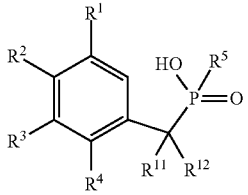

4. A method of preparing a compound characterized by performing an intramolecular carbon-oxygen coupling reaction on a phosphinic acid compound represented by the following Chemical Formula 7 to prepare a compound represented by the following Chemical Formula 3 in the presence of a palladium (Pd) catalyst, an oxidant, and a base:

[Chemical Formula 3]

[Chemical Formula 7]

in Chemical Formulas 3 and 7,
$R^1$ to $R^4$ are each independently hydrogen, (C1-C20)alkyl, halo(C1-C20)alkyl, (C1-C20)alkoxy, (C6-C20)aryl, halogen, (C6-C20)aryloxy, or tri(C1-C20)alkylsilyl;
$R^5$ is (C1-C20)alkyl, (C1-C20)alkoxy, or (C6-C20)aryl;
$R^{11}$ and $R^{12}$ are each independently (C1-C20)alkyl, or are linked to each other by (C1-C7)alkylene to form a spiro ring; and
the alkyl and aryl of $R^1$ to $R^5$ are optionally substituted with a substituent selected from the group consisting of halogen, (C1-C20)alkyl, (C1-C20)alkoxy, and halo(C1-C20)alkyl.

5. The method of preparing a compound of claim 4, wherein the palladium (Pd) catalyst is one or two or more selected from the group consisting of $PdCl_2$, $PdBr_2$, $Pd(OAc)_2$, $Pd(dba)_2$, $Pd_2(dba)_3$, $Pd_2dba_3 \cdot CHCl_3$, $Pd(PPh_3)_4$, $Pd(OTf)_2$, $Pd(OTf)_2 \cdot 2H_2O$, $Pd(TFA)_2$, $PdCl_2(MeCN)_2$, $PdCl_2(PPh_3)_2$, $Pd(dppf)Cl_2$, and $[PdCl(C_3H_5)]_2$.

6. The method of preparing a compound of claim 4, wherein a use amount of the palladium (Pd) catalyst is 0.01 to 0.5 equivalents with respect to the phosphinic acid compound represented by Chemical Formula 7.

7. The method of preparing a compound of claim 4, wherein the oxidant is one or two or more selected from the group consisting of CuCl, $Cu_2O$, CuO, $Cu(OAc)_2$, $Cu(OTf)_2$ [OTf: trifluoromethanesulfonate], $CuCl_2$, CuBr, CuI, Cu(acac)$_2$, $Ag_2O$, AgO, AgOAc, $Ag_2CO_3$, $Na_2S_2O_8$, $K_2S_2O_8$, NaOAc, BQ [BQ: benzoquinone], $FeCl_3$, $Mn(OAc)_3 \cdot 2H_2O$, $V_2O_5$, $PhI(OAc)_2$, $PhI(TFA)_2$, IOAc, ozone, oxygen, $(PhCO_2)_2$, and 2,2,6,6-tetramethyl-1-piperidinyloxy (free radical, TEMPO).

8. The method of preparing a compound of claim 4, wherein a use amount of the oxidant is 0.1 to 5.0 equivalents with respect to the phosphinic acid compound represented by Chemical Formula 7.

9. The method of preparing a compound of claim 4, wherein the base is one or two or more selected from the group consisting of $KH_2PO_4$, $Na_2HPO_4 \cdot 2H_2O$, $Na_2HPO_4$, $Na_2CO_3$, $NaH_2PO_4$, LiOAc, $Li_2CO_3$, NaOAc, $K_2HPO_4$, $K_3PO_4$, $K_2CO_3$, CsF, $KHCO_3$, KOH, KF, $KPF_6$, KOAc, NaF, CsOAc, CsOPiv, $LiPF_6$, $Li_3PO_4$, LiF, and LiI.

10. The method of preparing a compound of claim 4, wherein a use amount of the base is 0.5 to 3.0 equivalents with respect to the phosphinic acid compound derivative represented by Chemical Formula 7.

\* \* \* \* \*